(12) United States Patent
Imran et al.

(10) Patent No.: US 10,548,851 B2
(45) Date of Patent: Feb. 4, 2020

(54) METHODS AND ARTICLES FOR DELIVERING VIABLE CELLS INTO SOLID TISSUE

(71) Applicant: InCube Labs, LLC, San Jose, CA (US)

(72) Inventors: Mir Imran, Los Altos Hills, CA (US); Joel Harris, Mountain View, CA (US)

(73) Assignee: InCube Labs, LLC, San Jose, CA (US)

( * ) Notice: Subject to any disclaimer, the term of this patent is extended or adjusted under 35 U.S.C. 154(b) by 0 days.

(21) Appl. No.: 16/255,020

(22) Filed: Jan. 23, 2019

(65) Prior Publication Data

US 2019/0151250 A1 May 23, 2019

Related U.S. Application Data

(62) Division of application No. 15/455,080, filed on Mar. 9, 2017, now Pat. No. 10,220,003.

(60) Provisional application No. 62/305,878, filed on Mar. 9, 2016.

(51) Int. Cl.
| | | |
|---|---|---|
| *A61K 9/48* | (2006.01) |
| *A61K 35/12* | (2015.01) |
| *A61K 9/00* | (2006.01) |
| *A61B 5/00* | (2006.01) |
| *A61B 5/145* | (2006.01) |
| *A61M 31/00* | (2006.01) |
| *A61K 35/28* | (2015.01) |
| *A61K 35/30* | (2015.01) |
| *A61K 35/39* | (2015.01) |
| *A61K 9/06* | (2006.01) |
| *A61M 25/10* | (2013.01) |

(52) U.S. Cl.
CPC ........ *A61K 9/4816* (2013.01); *A61B 5/14507* (2013.01); *A61B 5/14539* (2013.01); *A61B 5/14546* (2013.01); *A61B 5/6861* (2013.01); *A61K 9/0053* (2013.01); *A61K 9/06* (2013.01); *A61K 9/4891* (2013.01); *A61K 35/12* (2013.01); *A61K 35/28* (2013.01); *A61K 35/30* (2013.01); *A61K 35/39* (2013.01); *A61M 25/1002* (2013.01); *A61M 31/002* (2013.01); *A61B 5/4255* (2013.01); *A61M 2025/105* (2013.01); *A61M 2205/3633* (2013.01)

(58) Field of Classification Search
CPC ..................................................... A61K 9/06
See application file for complete search history.

(56) References Cited

U.S. PATENT DOCUMENTS

| | | | |
|---|---|---|---|
| 8,721,620 B2 | 5/2014 | Imran |
| 8,734,429 B2 | 5/2014 | Imran et al. |
| 8,759,284 B2 | 6/2014 | Imran |
| 8,846,040 B2 | 9/2014 | Imran |
| 10,220,003 B2 | 3/2019 | Imran et al. |
| 2004/0253304 A1 | 12/2004 | Gross et al. |
| 2005/0267414 A1 | 12/2005 | Abraham-Fuchs et al. |
| 2010/0215715 A1 | 8/2010 | Han et al. |
| 2013/0095081 A1 | 4/2013 | March et al. |
| 2013/0171245 A1 | 7/2013 | Imran |
| 2014/0072601 A1 | 3/2014 | Connon et al. |
| 2014/0271767 A1 | 9/2014 | Askari et al. |
| 2015/0274805 A1 | 10/2015 | Annabi et al. |
| 2017/0258732 A1 | 9/2017 | Imran et al. |
| 2017/0258833 A1 | 9/2017 | Imran et al. |

FOREIGN PATENT DOCUMENTS

| | | |
|---|---|---|
| WO | WO-2016004068 A1 | 1/2016 |
| WO | WO-2017156347 A1 | 9/2017 |

OTHER PUBLICATIONS

EP17764157.8 Extended European Search Report dated Sep. 12, 2019.
Grikscheit, et al. Tissue-engineered small intestine improves recovery after massive small bowel resection. Ann Surg., 2004, 240:748-754.
International search report with written opinion dated Jun. 30, 2017 for PCT/US2017/021692.
Notice of allowance dated Oct. 25, 2018 for U.S. Appl. No. 15/455,080.
"Office Action dated May 22, 2018 for U.S. Appl. No. 15/455,080."
Sivashanmugam, et al. An overview of injectable polymeric hydrogels for tissue engineering. European Polymer Journal, 2015, 72:543:565.
Zhang, et al. Preliminary study on the freeze-drying of human bone marrow-derived mesenchymal stem cells. J Zhejiang Univ Sci B. Nov. 2010;11(11):889-94. doi: 10.1631/jzus.B1000184.

*Primary Examiner* — Bin Shen
(74) *Attorney, Agent, or Firm* — Wilson Sonsini Goodrich and Rosati, P.C.; Joel M. Harris

(57) ABSTRACT

Embodiments provide swallowable devices, preparations and methods for delivering viable cells (VC) into the GI tract including GI wall tissue or other tissue site. Particular embodiments provide a swallowable device such as a capsule for delivering VC into an intestinal wall or other site. The VC can be contained within a tissue-penetrating shell disposed in the capsule that protects the VC as they pass through the GI tract until they are inserted into GI tract tissue or other location. The shell desirably has shape, size and material consistency to be contained in a swallowable capsule, delivered from the capsule into solid tissue by the application of force on the shell and biodegrade within the solid tissue to release the VC into the tissue. Within the shell or other structure the VC can be maintained in a viability-sustaining gel that preserves the viability of the VC for selected time periods.

35 Claims, 42 Drawing Sheets

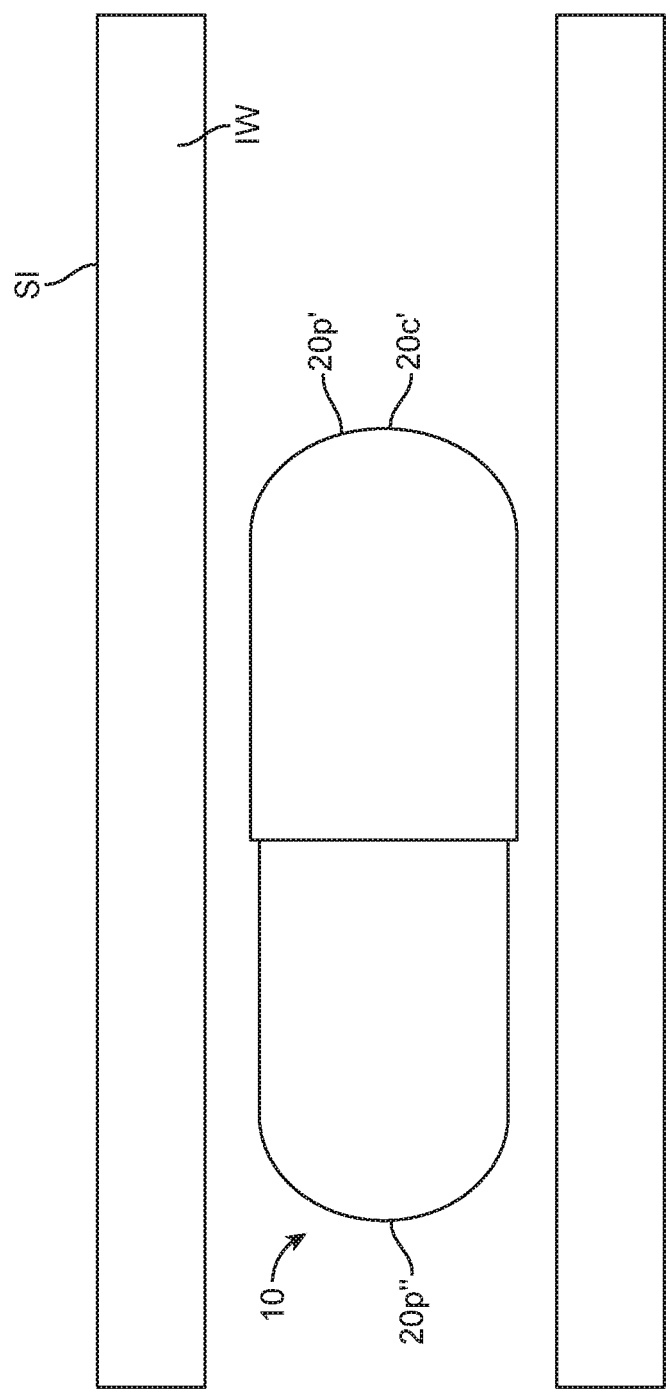

Deglutition

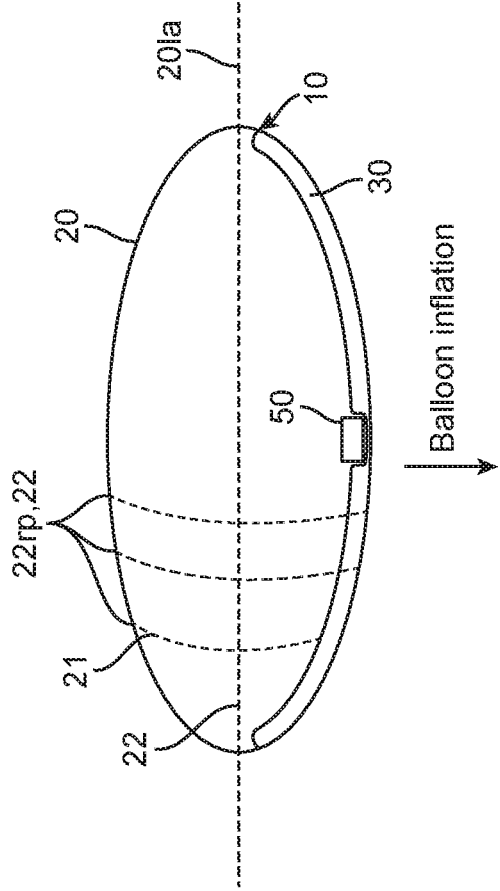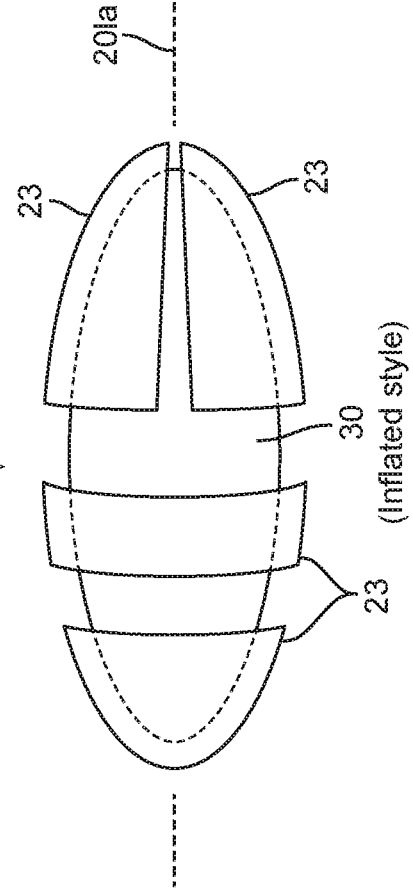

METHODS AND ARTICLES FOR DELIVERING VIABLE CELLS INTO SOLID TISSUE

CROSS-REFERENCE TO RELATED APPLICATIONS

This application is a divisional of U.S. patent application Ser. No. 15/455,080, filed Mar. 9, 2017, now U.S. Pat. No. 10,220,003, which claims the benefit of priority to Provisional U.S. patent application Ser. No. 62/305,878, filed Mar. 9, 2016; the entire contents of which are incorporated herein by reference.

This application is also related to co-filed U.S. patent application Ser. No. 15/455,075, the full disclosure of which is incorporated herein for all purposes. This disclosure of the application incorporates disclosure from U.S. patent application Ser. No. 13/837,025, now U.S. Pat. No. 8,734,429, filed Mar. 15, 2013, the entire contents of which are hereby incorporated by reference herein for all purposes.

BACKGROUND OF THE INVENTION

1. Field of the Invention

Embodiments of the invention relate to swallowable viable cells delivery devices. More specifically, embodiments of the invention relate to swallowable delivery devices for delivering viable cells to the small intestine and other solid tissues.

While there has been an increasing development of new viable cells in recent years for the treatment of a variety of diseases, many including proteins, antibodies and peptides have limited application because they cannot be given orally. This is due to a number of reasons including: poor oral toleration with complications including gastric irritation and bleeding; breakdown/degradation of the viable cells compounds in the stomach; and poor, slow or erratic absorption of the viable cells. Conventional alternative viable cells delivery methods such as intravenous and intramuscular delivery have a number of drawbacks including pain and risk of infection from a needle stick, requirements for the use of sterile technique and the requirement and associated risks of maintaining an IV line in a patient for an extended period of time. While other viable cells delivery approaches have been employed such as implantable viable cells delivery pumps, these approaches require the semi-permanent implantation of a device and can still have many of the limitations of IV delivery. Thus, there is a need for an improved method for delivery of viable cells and other therapeutic agents.

U.S. Pat. Nos. 8,721,620; 8,759,284; and 8,734,429, all commonly assigned with the present patent application, describe swallowable devices which are optimized for the delivery of proteins and other labile viable cells to a patient's intestines. While very effective for delivering viable cells formulations, these devices are not optimized for delivering living cells to a patient. The delivery of living or viable cells, such as stem cells, cells which secrete therapeutically beneficial agents, and the like, to a patient promises to be of enormous clinical benefit, but is hindered by a shortage of effective delivery apparatus, materials and protocols.

For these reasons, it would be desirable to provide improved and alternative apparatus, materials and protocols for the delivery of viable cells to human and animal patients. At least some of these objectives will be met by the inventions described and claimed herein.

2. Description of the Background Art

U.S. Pat. Nos. 8,721,620; 8,759,284; and 8,734,429 have been described above. See also US2013/0095081 and US 2010/0215715.

SUMMARY OF THE INVENTION

Embodiments of the present invention provide articles, methods, devices, and systems for delivering viable cells into solid tissue into the gastro intestinal tract and organs of digestion. The viable cells can be delivered for one or both of therapeutic and diagnostic purposes. The viable cells will typically be delivered to human patients but could also be delivered to other mammalian animals for veterinary purposes. The viable cells may include a variety of mammalian cells types such as pancreatic enteroendocrine cells, for example beta cells; Gastric enteroendocrine cells such as G-cells; or Intestinal enteroendocrine cells such as L-cells K-cells, I-cells, N-cells and S-cells. They may also include various mucosal cells, including for example, gastro-intestinal mucosal cells Viable cells being delivered will typically produce therapeutically beneficial agents, such as pancreatic beta cells which produce insulin; immune cells which produce proteins of the immune system, incretin producing cells such as L-cells, K-cells, and a variety of stem cells such as mesenchymal stem cells, hematopoietic stem cells, and the like. The cells will typically be delivered to the patient's intestinal tissue, usually via an oral delivery route where the viable cells pass through the gastrointestinal tract before being delivered to the intestinal tissue. A particular advantage of the present invention is that viability of the cells can be maintained as the cells pass through the gastrointestinal tract prior to delivery into the intestinal tissue, the delivery of which can take many hours during which the viability of the cells is at risk.

In a first aspect, the present invention provides articles for delivering viable cells into solid tissue. The articles include a shell configured for self-penetration into the solid tissue, typically having a sharpened, pointed, conical, or other conventional tissue-penetrating tip. In other embodiments, the self-penetrating tip may include an electrosurgical element (e.g. and RF energy powered element) to enhance penetration into tissue. A mass of viable therapeutic cells is maintained within an interior of the shell under conditions which promote viability. In particular embodiments, cells will usually be maintained in preparation including a viability-sustaining gel, such as an alginate gel, a protein gel, a glycosaminoglycan gel, a carbohydrate gel, or other conventional gel or medium known for maintaining mammalian cell viability. In particular embodiments the gel can be saturated or partially saturated with oxygen to provide further viability sustaining qualities to the gel. This may be done before or after addition of the cells to the gel. Once penetrated or otherwise placed into tissue, the article is configured to degrade (also referred to as biodegrade) in tissue to release the mass of viable cells into tissue.

In certain embodiments, the shell of the article will be configured to biodegrade over a time period of at least 12 hours, i.e. the shell will not degrade during the initial 12 hours it is within the patient gastrointestinal tract or elsewhere. Often, the time period for degradation is in the range from 4 hours to one year, typically being from ½ days to 5 days with specific embodiments of 1, 2, 3, 4 days. Often, it will be an objective of the present invention to maintain the shell only for so long as necessary to protect the cells from passage through the gastrointestinal tract and to release the shells from containment as quickly as possible after implantation into the intestinal wall or other location.

A variety of specific materials may be used for the biodegradable shells, including biodegradable metals, such as magnesium, iron, and zinc. Biodegradable polymers will also be useful, including, for example, poly lactic acid (PLA), poly lactic-co-glycolic acid (PLGA) and various sugars such as maltose, sucrose and the like. Further according to one or more embodiments the shell may comprise multiple layers of the same or different materials with the layers configured to degrade at different rates (e.g. hours vs days). In use such embodiments allow for a rapid release of cells followed for example for the rapid generation of a particular therapeutic substance such as insulin, followed by a longer term release to allow for the longer term release. For embodiments of the article configured for the treatment of diabetes or other glucose regulation disorder this allows for a short term and longer term treatment of the disease or condition. The variation in the degradation rates can be controlled by selection of one or more of the thickness, surface area, material and material properties of the shell.

In certain embodiments, the shell of the delivery article may have fenestrations, e.g., holes, apertures, or other small passages formed there through. The fenestrations will be configured to allow passage of fluids and small molecules into and out of an interior of the shell, but to contain the cells and the gel within the interior of the shell. In various embodiments the fenestrations can have a diameter a selected diameter matched to a selected percentage (e.g., 1, 5, 10, 25, 50% etc.) to the major diameter of the particular cell or cells contained within the article. The fenestrations will typically have a width in the range from about 0.1 to 15 µm more preferably about 0.5 to 5 µm and/or an area in the range from 0.03 to 700 µm$^2$ more preferably about 0.8 to 80 µm$^2$. When the shell comprises fenestrations, it may be formed from a non-biodegradable material since many cells can maintain viability through fluid and substance exchange with the implanted tissue and can release therapeutically useful cell products to the tissue through the same fenestrations. Usually, however, even with fenestrations, it will be preferable to form the wall from the biodegradable material. In an alternative or additional embodiment the fenestrations may be configured to produce a distinct acoustical signature or pattern when pinged by an external acoustical transceiver such as an ultrasound transceiver or other piezo electric based acoustical transceiver. Further as the fenestrations break down due to bioerosion of the article the acoustical signature of shell in response to the ping changes such the degree of bio-erosion of the shell can be discerned. In particular embodiments the fenestrations can be configured to produce distinct acoustical patterns when there is no bio-erosion, and when there is 25, 50 and 75% bio-erosion. In this way, the fenestrations provide actionable information for the user to know when the article has degraded sufficiently to release the cells to the selected tissue site. The specific acoustical signatures can be produced by the size and spacing of the fenestrations. In alternative or additional embodiments for providing information on the state of degradation of the articles, the articles can include acoustical markers or indicia configured to provide specific acoustical signatures of the percent degradation of the article.

In a second aspect, the present invention provides methods for delivering viable cells into solid tissues such as the tissue in the walls of the intestinal tract such as the small intestine and/or the digestive organs such as the pancreas. The methods comprise administering an article to a patient, such as a tissue penetrating member, where the article contains a selected mass or volume of therapeutic cells in a viable state. Typically, the mass of cells will be contained in preparation comprising the cells and a viability sustaining gel described herein. The article is then penetrated into the solid tissue, and at least a portion of the article biodegrades to release the cells within the tissue in a viable state. The cells are then available to produce therapeutically useful agents and substances which can be released directly into the tissue in which the cells have been implanted. In certain embodiments of this method, administering comprises the patient swallowing the article, which may be contained in swallowable capsule described herein, where the article passes through the patient's gastrointestinal tract and into the patient's intestines. Once resident in the intestines, the article will be propelled into the intestinal wall by operative coupling with an expansion means such as an expandable balloon that contains chemical reactants which produce a gas upon being mixed so to expand the balloon. Typically, this will be done response to a pH change within the intestines, such as the higher pH in the small intestine, where said pH change triggers the chemical reaction which results in propulsion of the article into the intestinal wall. Other means for generating a propulsive force so at to have the article penetrate and be inserted into the intestinal wall are also contemplated. For example, a propulsive force may be generated through the use of an electromagnetic force (from piezo electro material), a hydrostatic force or a spring force.

In a third aspect, the invention provides methods for delivering viable cells into solid tissues such as the tissue in the walls of the intestinal tract wherein the cells are put into a reversible suspended state of animation prior to being administered to the patient (including prior to being put into the article) wherein they reanimate after being delivered to the patient so as to produce a therapeutic effect. Such therapeutic effects can include for example the cellular production of one or more therapeutic compounds (e.g., insulin, integrins, etc.). Typically, this will be done by freezing or chilling the cells and/or the gel containing them within the article prior to administering the article to the patient. Chilling may be done to a temperature in the range of 50 to 33° F. with a preferred range of 39 to 40° F. In an alternative or variation, the cells and/or gel containing them may be frozen or chilled prior to being placed into the article. Freezing or chilling the articles and the cells therein prior to administration is particularly useful as it can preserve the cells for extended periods of time in a reversible state of suspended animation without the need to supply nutrients and remove cellular products. Once articles are administered to the patient, however, the cells will thaw and warm within a short time period to become reanimated and will resume cellular processes and may be at risk of degradation from the gastrointestinal environment. The shell of the article, as described above, will protect the now metabolically active cells as they pass through a patient's gastrointestinal tract where they would be exposed to the digestive conditions of the stomach which, without protection, would damage or kill the cells. Once penetrated into the intestinal tract, the article will be implanted into the intestinal tissue, thus releasing the viable cells where they are now in an environment in which cell viability can be maintained and they can generate the useful therapeutic substances which they produce. Embodiments of these methods employ articles which may have the preferred characteristics and dimensions discussed above in connection with articles of the present invention. Other methods of suspended reversible animation of the viable cells are also contemplated besides freezing and chilling. These may include for example, use of certain compounds in the gel and/or charging the gel with an inert gas (e.g., nitrogen) and lyophilizing of the cells (or other freeze drying methods) prior to administration.

As discussed above for embodiments where the cells are orally delivered, the frozen, chilled or otherwise suspended cells pass through the patient's gastrointestinal tract and are protected from conditions of the gastrointestinal tract by a barrier provided by the article. The barrier remains intact while the article passes through gastrointestinal tract, but the barrier will erode over time within the intestinal tissue to release the cells and/or therapeutically beneficial cellular products over time. In use, such methods allow for the long term storage of the cells allowing the patient to store the articles containing the cells at home and take them over an extended period of weeks to months. In embodiments where the cells are frozen or chilled, the article itself can be configured to be frozen. In particular embodiments it can be configured to be frozen without undergoing cracking or other structural deformations which may compromise the barrier function of the article. Further the space in the article interior may be increased relative to articles containing non frozen cells so as to account for any expansion of the gel or other medium containing the cells due to freezing so that the article as well the cells are not damaged during freezing. Alternatively, the article interior may be only partially filled to provide for expansion of the gel during freezing. These specific materials and dimensions of the article's use in this second method are also described in more detail with respect to the articles of the present invention.

In a fourth aspect, the invention provides a method whereby the patient can take a regimen of swallowable articles containing viable cells over a period of days, weeks or months so as to achieve a desired therapeutic effect. For example, the patient may take a regimen of articles containing various doses of L-cells or K-cells to reestablish incretin production in the small intestine over a period of time and in turn glucose regulation or G-cells to reestablish the production of gastrin in the stomach or small intestine over a period of time so as to improve one or more of acid production, mucosal architecture and cell differentiation in the GI tract including the stomach, small and large intestine. The regimen may include varying the doses over the period of time including for example an initial dose followed by lower maintenance doses. These specific materials and dimensions of the article's use in this second method are also described in more detail with respect to the articles of the present invention.

In a fifth aspect, the invention provides methods whereby the patient takes swallowable articles containing viable cells to reseed selected portions of the GI tract with cells such as hormone or other peptide producing cells that produce a desired therapeutic effect. For example, L-cells or K-cells to produce incretin or G-cells to produce Gastrin. In specific embodiments, the cells can comprise various mucosal cells to reseed the mucosa of the stomach, pylorus and duodenum to treat one or more of a gastric, pyloric or duodenal ulcer. Further the articles can be configured to reseed specific portions of specific GI organs such as the duodenum or jejunum of the small intestine and the pyloric region of the stomach. The articles can be configured to inject cells into theses specific regions by the use of pH sensitive coatings described herein such as various EUDRAGIT coatings and others known in the art which degrade in response to specific pH's in specific location, such as more acid pH in the stomach (1.5-3.5) and increasingly less acidic pH in the small intestine (5.5 in the duodenum and 6.5-6.8 in the jejunum).

Further details of these and other embodiments and aspects of the invention are described more fully below, with reference to the attached drawing figures.

BRIEF DESCRIPTION OF THE DRAWINGS

FIG. 2A shows the capsule in an unassembled state and FIG. 2B in an assembled state.

FIG. 3A shows an embodiment of the assembly for a single dome configuration of the deployment balloon; and FIG. 3B shows an embodiment of the assembly for dual dome configuration of the deployment balloon;

FIG. 4A shows the balloon in a non-inflated state with the separation valve closed; FIG. 4B shows the balloon with valve open and mixing of the chemical reactants; and FIG. 4C shows the balloon in an inflated state.

FIG. 5D, pertains to the final folding step unique to dual dome configurations; FIG. 5E, pertains to a folding step unique to single dome configurations; and FIGS. 5F and 5G are orthogonal views pertaining to the final folding step unique to single dome configurations.

FIGS. 10A-10I provide assorted views illustrating a method of operation of swallowable device to deliver viable therapeutic cells to the intestinal wall.

FIGS. 15A-15B show an embodiment of a capsule having tearable seams arranged in a radial or lateral pattern for tearing of the capsule by inflation of the expandable balloon; FIG. 15A shows the capsule prior to inflation and FIG. 15B shows the capsule broken into pieces by the inflation of the balloon.

DETAILED DESCRIPTION OF THE INVENTION

Figure 1A:
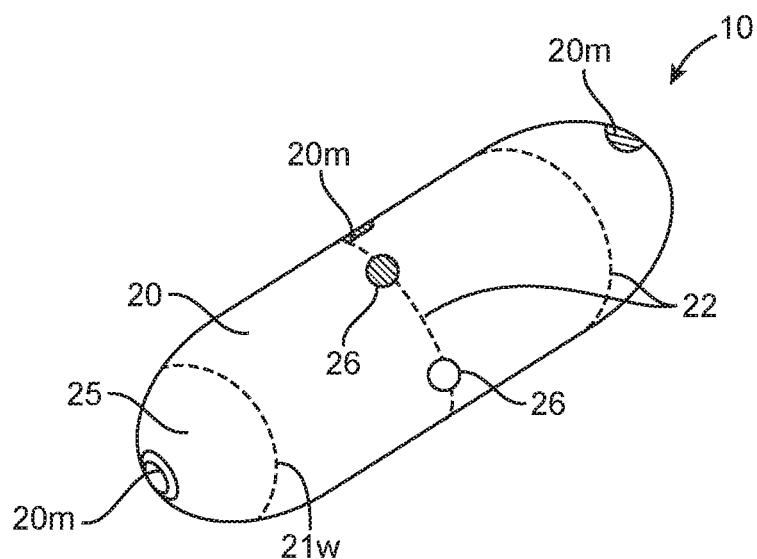
FIG. 1A is a lateral viewing showing an embodiment of a swallowable viable cells delivery device.

Embodiments of the invention provide devices, preparations, systems and methods for delivering viable cells in to various locations in the body, in particular to the intestinal wall tissue. In many embodiments the cells will be delivered by a swallowable device configured to maintain viability of the cells while they pass through the gastrointestinal tract and to a selected site within intestinal tract or other location. As used herein, "GI tract" refers to the esophagus, stomach, small intestine, large intestine and anus, while "Intestinal tract" refers to the small and large intestine. Various embodiments of the invention can be configured and arranged for delivery of viable cells into the intestinal tract as well as the entire GI tract. Also in many embodiments the delivered cells will comprise therapeutic cells and will sometimes be referred to as such. However embodiments of the invention are not limited to therapeutic cells only. In particular it should be understood that the delivered cells may also comprise cells used for diagnostic purposes. Also in various embodiments, the term preparation 100 is used to described a preparation comprising viable cells 101 including viable therapeutic cells. Preparation 100 will sometimes be referred to as a "viable cell preparation", "cell preparation" or just "preparation" 100 with all three being interchangeable. Further in addition to viable cells 101, in various embodiments, preparation 100 may comprise one or more drugs or other therapeutic agents, diagnostics agents, and various excipients described herein and known in the art. In particular embodiments, preparation 100 also includes a viability preserving gel 49 as is described herein.

Referring now to FIGS. 1-9, an embodiment of a device 10 for the delivery of a preparation 100 comprising viable cells 101 to a delivery site DS in the gastro-intestinal (GI) tract, comprises a capsule 20 sized to be swallowed and pass through the intestinal tract, a deployment article 30, one or more tissue penetrating articles 40 (also referred to as shell 40) containing a cell preparation 100 comprising viable therapeutic cells 101, a deployable aligner 60 and a delivery mechanism 70. It should be appreciated that this is but one embodiment of a device for the delivery of viable cells 101 and that other embodiments described herein are equally applicable including devices without an aligner balloon 60.

The deployable aligner 60 is positioned within the capsule and configured to align the capsule with the intestine such as the small intestine. Typically, this will entail aligning a longitudinal axis of the capsule with a longitudinal axis of the intestine; however, other alignments are also contemplated. The delivery mechanism 70 is configured for delivering cell preparation 100 containing viable therapeutic cells 101 into the intestinal wall and will typically include a delivery article 72 such as an expandable member. The deployment member 30 is configured for deploying at least one of the aligner 60 or the delivery mechanism 70. As will be described further herein, all or a portion of the capsule wall is degradable by contact with liquids in the GI tract so as to allow those liquids to trigger the delivery of viable cells 101 by device 10. As used herein, the term "GI tract" refers to the esophagus, stomach, small intestine, large intestine and anus, while "Intestinal tract" refers to the small and large intestine. Various embodiments of the invention can be configured and arranged for delivery of preparation 100 comprising viable therapeutic cells 101 into both the intestinal tract as well as the entire GI tract. Still other delivery cites are also considered including various intramuscular sites.

Device 10 including tissue penetrating article 40 can be configured for the delivery of liquid, semi-liquid or solid forms of preparation 100 comprising viable cells 101 or combinations of all three. Whatever the form, article 40 desirably has a size, shape and material consistency allowing the article to protect the viability of the cells 101 from the external environment (including that in the patient's GI tract prior to delivery); to be disposed in device 10/capsule 20; advanced out of device 10 into the intestinal wall (small or large intestine), peritoneal wall or other wall or tissue site in the GI tract; and then, degrade (e.g. biodegrade) within the intestinal wall to release the viable cells 101 or other therapeutic agent. The material consistency of article 40 can to performs these functions include one or more of the following: hardness, porosity and solubility of the material components comprising article 40 in bodily fluids (e.g., interstitial fluids) The material consistency can be achieved by selection and use of one or more of the following properties and/or characteristics of the article: i) the compaction force used to make the article; ii) the use of one or more pharmaceutical disintegrants known in the art; iii) use of other pharmaceutical excipients; iv) the particle size and particle distribution within the article (e.g., the use of micronized particles); and v) use of micronizing and other particle formation methods known in the art.

Figure 1B:
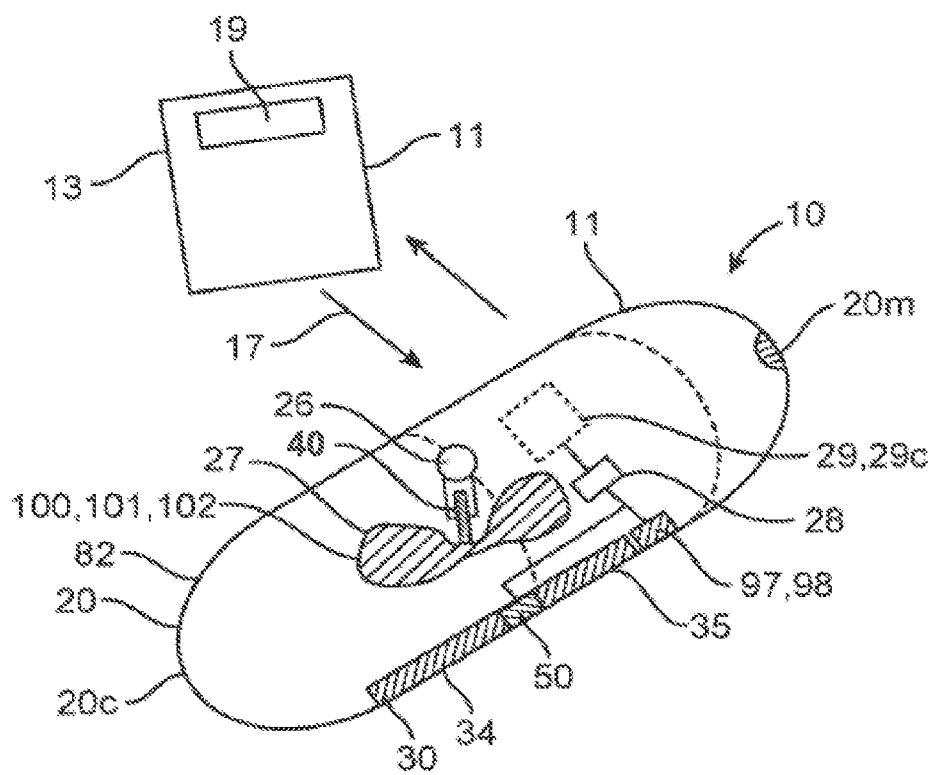
FIG. 1B is a lateral viewing showing an embodiment of a system including a swallowable viable cells delivery device.

Typically, the device 10 and/or preparation 100 will be configured to deliver a single type of cell 101 as part of preparation 100. However in some embodiments, device 10 preparation 100 can be configured for delivery of multiple cell types 101 including a first, second, or a third cell type which can be compounded into a single or multiple cell preparations 100. For embodiments having multiple cell types, each cell type 101 can be contained in separate tissue penetrating members 40 or within separate compartments or reservoirs 27 within capsule 20. In another embodiment, a first dose 102 of cell preparation 100 containing a cell type 101 can be packed into the penetrating member(s) 40 and a second dose 103 of cell preparation 100 (containing the same or a different cell 101) can be coated onto the surface 25 of capsule as is shown in the embodiment of FIG. 1B. The cell types 101 in the two doses of preparations 102 and 103 can be the same or different. In this way, a bimodal pharmacokinetic release of the same or different cells can be achieved.

Figure 1C:
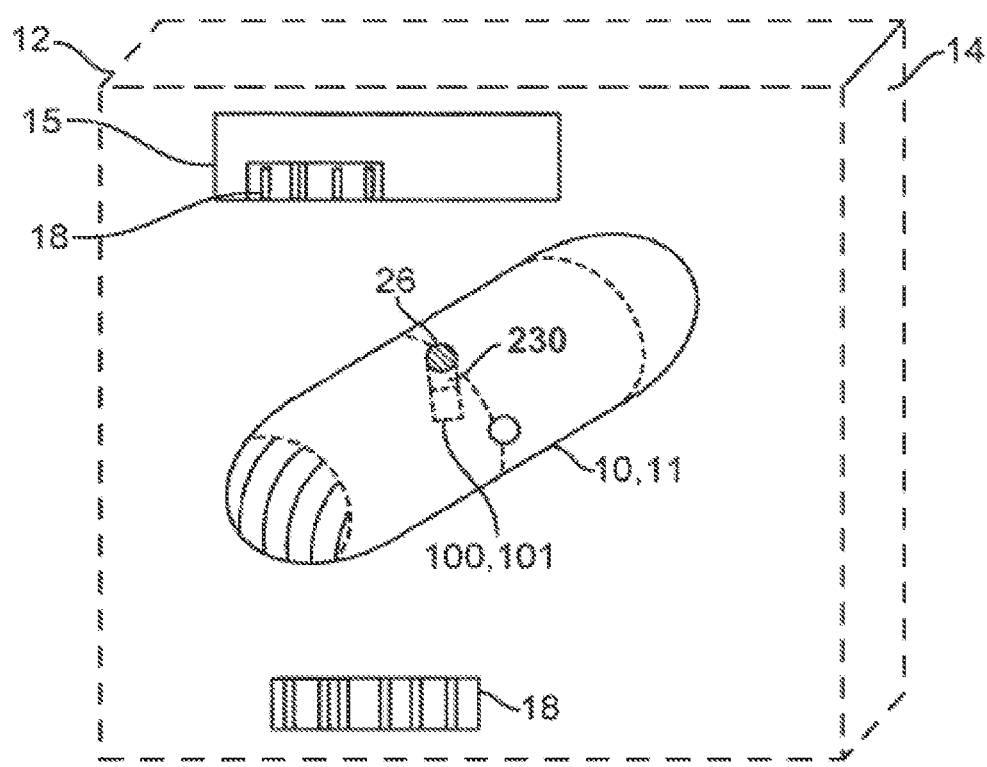
FIG. 1C is a lateral viewing showing an embodiment of a kit including a swallowable viable cells delivery device and a set of instructions for use.
Figure 1D:
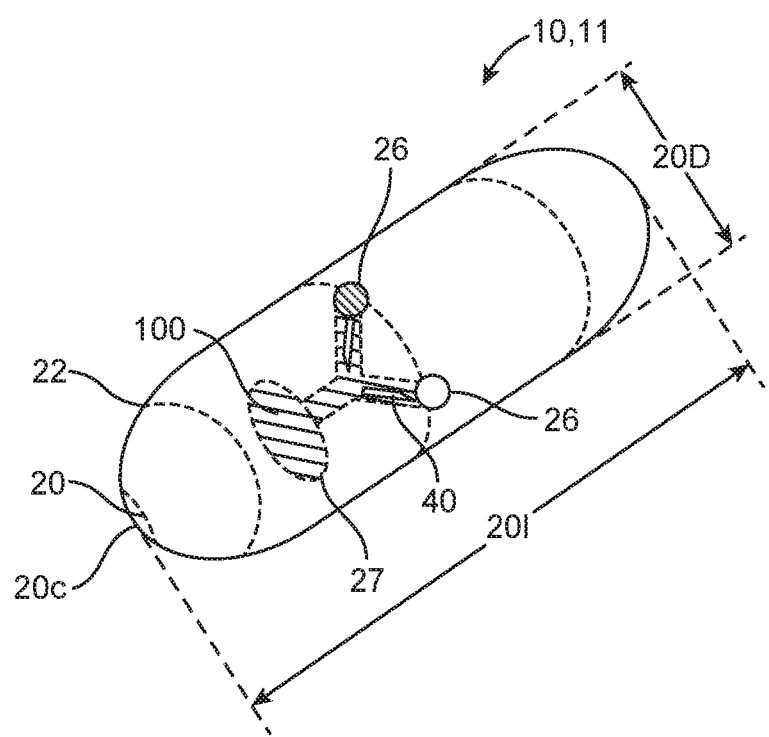
FIG. 1D is a lateral viewing showing an embodiment of a swallowable viable cells delivery device including a viable cells reservoir.
Figure 1E:
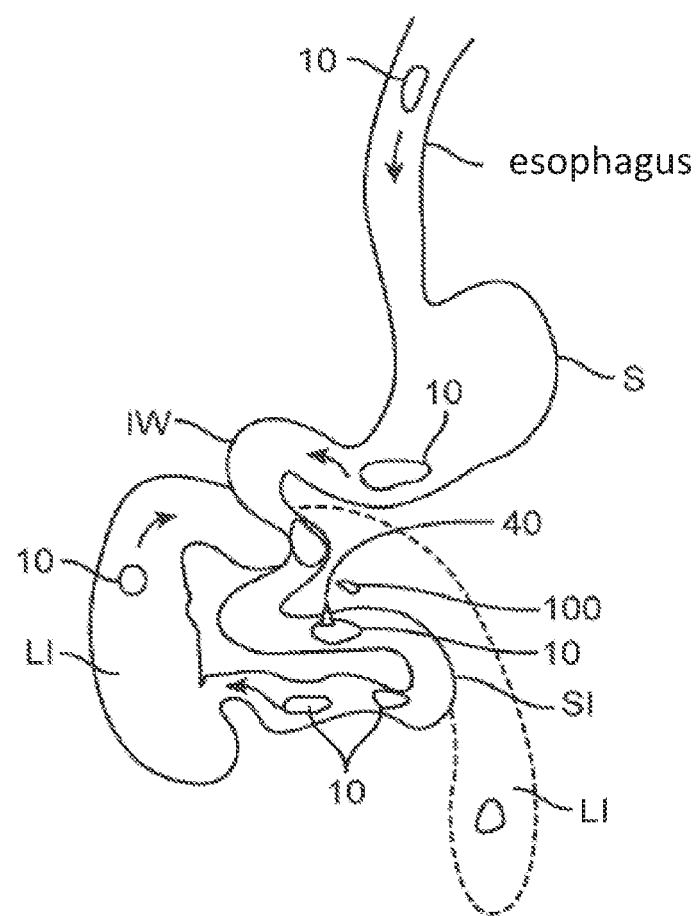
FIG. 1E is a lateral viewing illustrating use of an embodiment of a swallowable viable cells delivery device including transit of device in the GI tract and operation of the device to deliver viable cells.
Figures 2A, 2B:
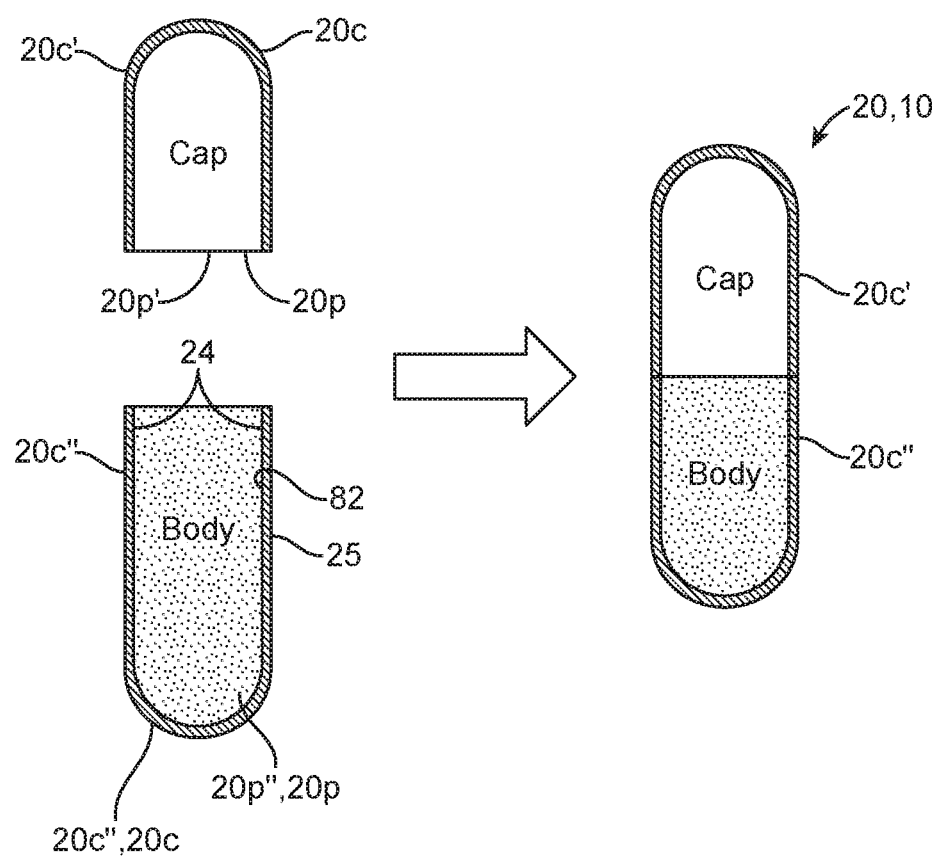
FIGS. 2A and 2B are lateral views illustrating an embodiment of a capsule for the swallowable viable cells delivery device including a cap and a body coated with pH sensitive biodegradable coatings.

In one or more embodiments, a system 11 for delivery of viable therapeutic cells 101 into the wall of the small intestine or other location within the intestinal tract or GI tract, may comprise device 10 and an article 40 which contains preparations 100 comprising one or more viable therapeutic cell types 101 for the treatment of a selected disease, condition or conditions. In some embodiments, the system may include a hand held device 13, described herein for communicating with device 10 as is shown in the embodiment of FIG. 1B. In many embodiments, system 11 may also be configured as a kit 14 including system 11 and a set of instructions for use 15 which are packaged in packaging 12 as is shown in the embodiment of FIG. 1C. The instructions can indicate to the patient when to take the device 10 relative to one or more events such as the ingestion of a meal or a physiological measurement such as blood glucose, cholesterol, etc. In such embodiments, kit 14 can include multiple devices 10 containing a regimen of viable therapeutic cells 101 for a selected period of administration, e.g., a day, week, or multiple weeks depending upon the condition to be treated (e.g., treatment of cancer by a course of interferon treatment, treatment of an autoimmune disease such as or psoriasis, multiple sclerosis or arthritis by immune suppression agents).

According to various embodiments, capsule 20 is sized to be swallowed and pass through the intestinal tract. The size can also be adjusted depending upon the amount of viable cells to be delivered as well as the patient's weight and adult vs. pediatric applications. Typically, the capsule will have a tubular shape with curved ends similar to a vitamin. In these and related embodiments, capsule lengths 20L can be in the range of 0.5 to 2 inches and diameters 20D in the range of 0.1 to 0.5 inches with other dimensions contemplated. The capsule 20 includes a capsule wall 21w, having an exterior surface 25 and an interior surface 24 defining an interior space or volume 24v. In some embodiments, the capsule wall 21w can include one or more apertures 26 sized for the outward advancement of tissue penetrating articles 40 via needle lumen 230. In addition to the other components of device 10, (e.g., the expandable member etc.), the interior volume can include one or more compartments or reservoirs 27.

The capsule can be fabricated from various biodegradable gelatin materials known in the pharmaceutical arts, but can also include various enteric coatings 20c, configured to protect the cap from degradation in the stomach (due to acids etc.), and then subsequently degrade in the in higher pH's found in the small intestine or other area of the intestinal tract. In various embodiments, the capsule 20 can be formed from multiple portions one or more of which may be biodegradable. In many embodiments, capsule 20 can be formed from two portions 20p such as a body portion 20p" (herein body 20p") and a cap portion 20p' (herein cap 20p'), where the cap fits onto the body, e.g., by sliding over or under the body (with other arrangements also contemplated). One portion such as the cap 20p' can include a first coating 20c' configured to degrade above a first pH (e.g., pH 5.5) and the second portion such as the body 20p" can include a second coating 20c" configured to degrade above a second higher pH (e.g. 6.5). Both the interior 24 and exterior 25 surfaces of capsule 20 are coated with coatings 20c' and 20c" so that that either portion of the capsule will be substantially preserved until it contacts fluid having the selected pH. For the case of body 20p" this allows the structural integrity of the body 20p" to be maintained so as to keep balloon 72 inside the body portion and not deployed until balloon 30 has expanded. Coatings 20c' and 20c" can include various methacrylate and ethyl acrylate based coatings such as those manufactured by Evonik Industries under the trade name EUDRAGIT. These and other dual coating configurations of the capsule 20 allows for mechanisms in one portion of capsule 20 to be actuated before those in the other portion of the capsule. This is due to the fact that intestinal fluids will first enter those portions where the lower pH coating has degraded thus actuating triggers which are responsive to such fluids (e.g., degradable valves). In use, such dual coating embodiments for capsule 20 provide for targeted viable cells delivery to a particular location in the small intestine (or other location in the GI tract), as well as improved reliability in the delivery process. This is due to the fact that deployment of a particular component, such as aligner 60, can be configured to begin in the upper area of the small intestine (e.g., the duodenum) allowing the capsule to be aligned within the intestine for optimal delivery of the viable cells (e.g., into the intestinal wall) as well as providing sufficient time for deployment/actuation of other components to achieve viable cells delivery into the intestinal wall while the capsule is still in the small intestine or other selected location.

As is discussed above, one or more portions of capsule 20 can be fabricated from various biocompatible polymers known in the art, including various biodegradable polymers which in a preferred embodiment can comprise cellulose, gelatin materials (PLGA) (polylactic-co-glycolic acid). Other suitable biodegradable materials include various enteric materials described herein as well as lactide, glycolide, lactic acid, glycolic acid, para-dioxanone, caprolactone, trimethylene carbonate, caprolactone, blends and copolymers thereof.

Use of biodegradable materials for capsule 20, including biodegradable enteric materials allows the capsule to degrade in whole or part to facilitate passage through the GI system before, during or after viable cells delivery. As is described in further detail herein, in various embodiments, capsule 20 can include seams 22 of bio-degradable material so as to controllably degrade into smaller pieces 23 which are more easily passed through the intestinal tract.

In various embodiments, the wall 20w of the capsule is degradable by contact with liquids in the GI tract for example liquids in the small intestine. In preferred embodiments, the capsule wall is configured to remain intact during passage through the stomach, but then to be degraded in the small intestine. In one or more embodiments, this can be achieved by the use of an outer coating or layer 20c on the capsule wall 20w, which only degrades in the higher pH's found in the small intestine and serves to protect the underlying capsule wall from degradation within the stomach before the capsule reaches the small intestine (at which point the viable cells delivery process is initiated by degradation of the coating as is described herein). In use, such coatings allow for the targeted delivery of a therapeutic agent in a selected portion of the intestinal tract such as the small intestine.

In various embodiments, capsule 20 can include various radio-opaque, echogenic or other materials for location of the device using one or more medical imaging modalities such as fluoroscopy, ultrasound, MRI, etc. In specific embodiments, all or a portion of the capsule can include radio-opaque/echogenic markers 20m as is shown in the embodiment of FIGS. 1A and 1B. Suitable materials for radio-opaque markers 20m include barium sulfate, compounds, titanium dioxide and compounds thereof. In use, such materials allow for the location of device 10 in the GI tract, as well as its state of deployment (e.g., a distinctive marker can be positioned on cap 20p' and another on body 20p" allowing for determination if the deployment balloon 30 (discussed below) has inflated but the delivery balloon 72 has not). They can also be used allow for the determination of transit times of the device through the GI tract. Such information can be used to titrate dosages of viable cells for a particular patient, as well as provide information on when they should take particular viable cells after an event such as ingestion of a meal in the case of insulin taken for treatment of diabetes. Markers 20m can also be positioned on the capsule 20 to allow the physician to determine if the capsule is intact, or has broken up.

As is discussed further herein, in many embodiments, one or more of the deployment member 30, delivery member 72 or deployable aligner 60, may correspond to an expandable balloon that is shaped and sized to fit within capsule 20. Accordingly, for ease of discussion, deployment member 30, delivery member 72 and deployable aligner 60 will now be referred to as balloon 30, 60 and 72; however, it should be appreciated that other devices including various expandable devices are also contemplated for these elements and may include for example, various shape memory devices (e.g., an expandable basket made from shape memory biodegradable polymer spires), expandable piezo electric devices, and/or chemically expandable devices having an expanded shape and size corresponding to the interior volume 24v of the capsule 20.

One or more of balloons 30, 60 and 72 can comprise various polymers known in the medical device arts. In preferred embodiments such polymers can comprise one or more types of polyethylene (PE) which may correspond to low density PE (LDPE), linear low density PE (LLDPE), medium density PE (MDPE) and high density PE (HDPE) and other forms of polyethylene known in the art. In one more embodiments using polyethylene, the material may be cross-linked using polymer irradiation methods known in the art. In particular embodiments radiation-based cross-linking may be used as to control the inflated diameter and shape of the balloon by decreasing the compliance of the balloon material. The amount or radiation may be selected to achieve a particular amount of cross linking to in turn produce a particular amount of compliance for a given balloon, e.g., increased irradiation can be used to produce stiffer less compliant balloon material. Other suitable polymers can include PET (polyethylene terephthalate), silicone and polyurethane. In various embodiments balloons 30, 60 and 72 may also include various radio-opaque materials known in the art such as barium sulfate to allow the physician to ascertain the position and physical state of the balloon (e.g., un-inflated, inflated or punctures. Balloons 30, 60 and 72 can be fabricated using various balloon blowing methods known in the balloon catheters arts (e.g., mold blowing, free blowing, etc.) to have a shape and size which corresponds approximately to the interior volume 24v of capsule 20. In various embodiments one or more of balloons 30, 60 and 72 and various connecting features (e.g., connecting tubes) can have a unitary construction being formed from a single mold. Embodiments employing such unitary construction provide the benefit of improved manufacturability and reliability since fewer joints must be made between one or more components of device 10.

Figure 3A:
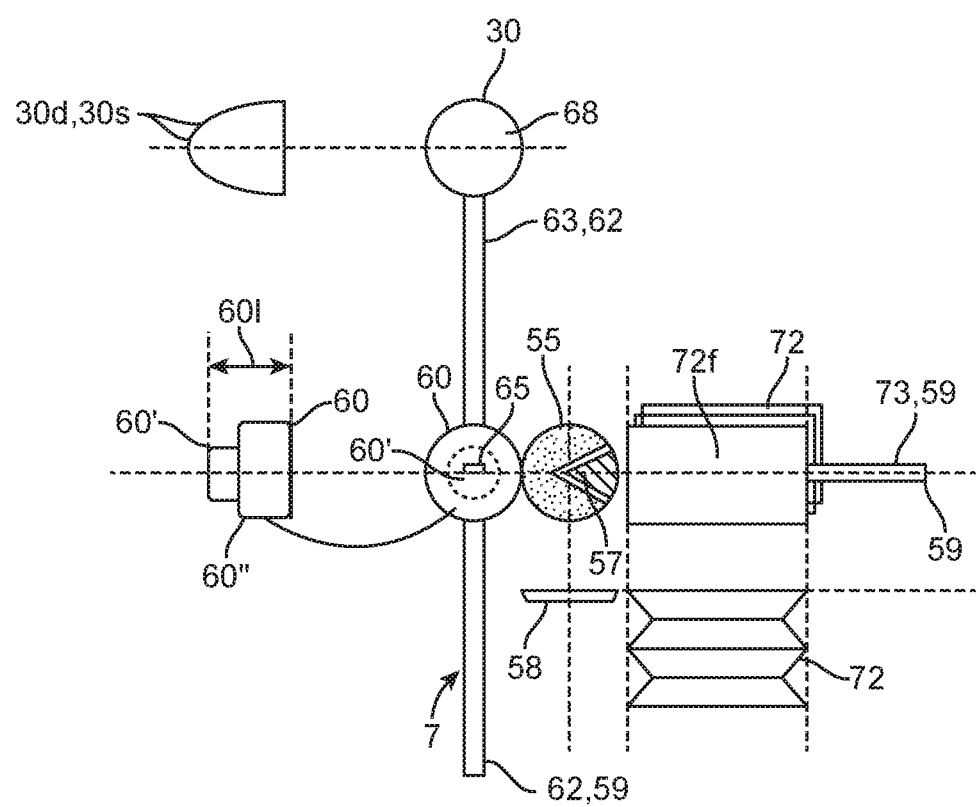
FIGS. 3A and 3B illustrate embodiments of unfolded multi balloon assemblies containing a deployment balloon, an aligner balloon, a delivery balloon and assorted connecting tubes.
Figure 3B:
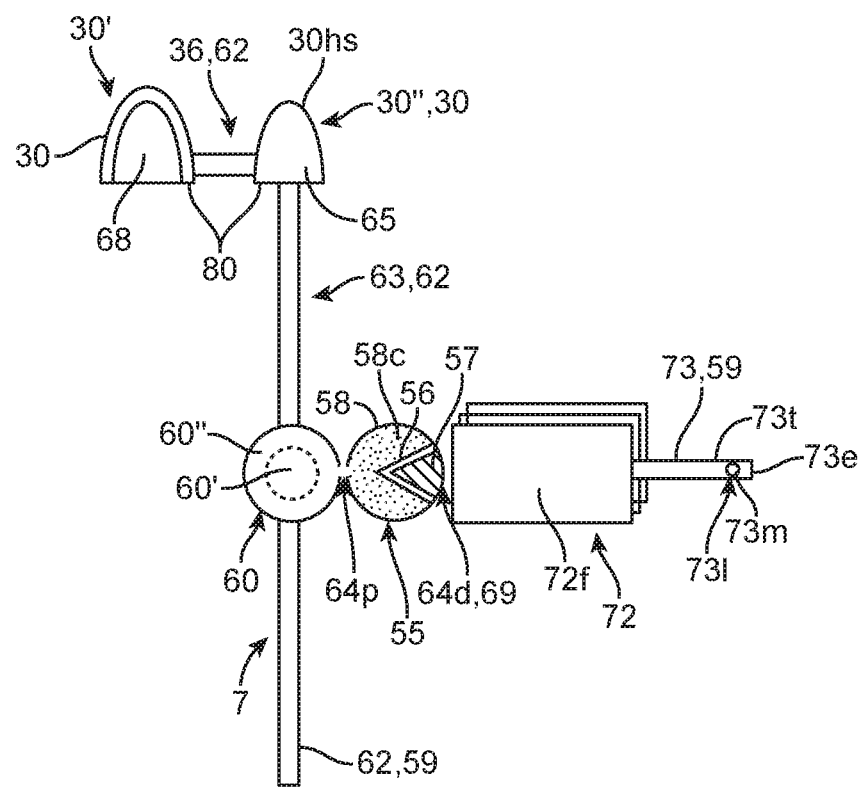
Figure 3C:
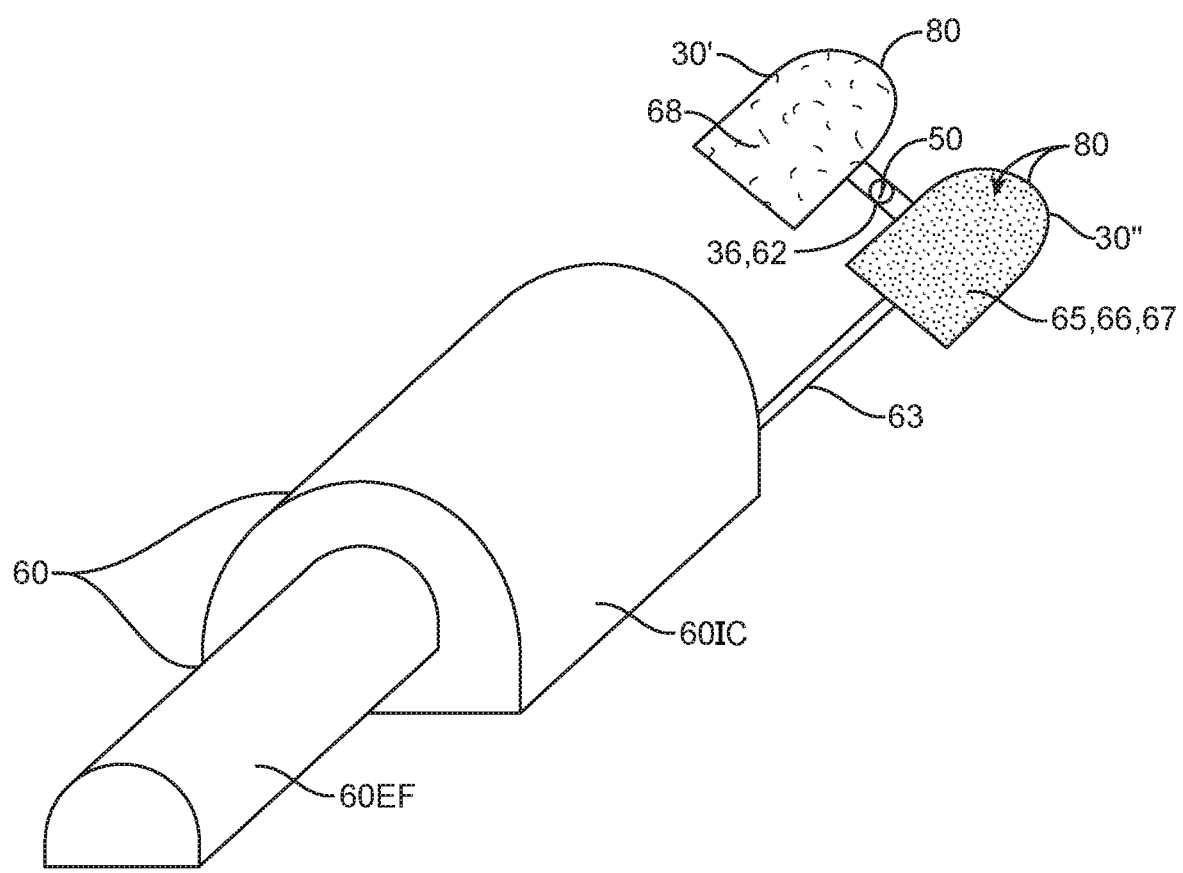
FIG. 3C is a perspective views illustrating embodiments of a nested balloon configuration which can be used for one or more embodiments of the balloons described herein including the aligner balloon.

Suitable shapes for balloons 30, 60 and 72 include various cylindrical shapes having tapered or curved end portions (an example of such a shape including a hot dog). In some embodiments, the inflated size (e.g., diameter) of one or more of balloons 30, 60 and 72, can be larger than capsule 20 so as to cause the capsule to come apart from the force of inflation, (e.g., due to hoop stress). In other related embodiments, the inflated size of one or more of balloons 30, 60 and 72 can be such that when inflated, i) the capsule 20 has sufficient contact with the walls of the small intestine so as to elicit a peristaltic contraction causing contraction of the small intestine around the capsule, and/or ii) the folds of the small intestine are effaced to allow contact. Both of these results allow for improved contact between the capsule/balloon surface and the intestinal wall so as deliver tissue penetrating articles 40 over a selected area of the capsule and/or delivery balloon 72. Desirably, the walls of balloons 30, 60 and 72 will be thin and can have a wall thickness in the range of 0.005 to 0.0001" more preferably, in the range of 0.005 to 0.0001, with specific embodiments of 0.004, 0.003, 0.002, 0.001, and 0.0005). Additionally in various embodiments, one or more of balloon 30, 60 or 72 can have a nested balloon configuration having an inflation chamber 60IC and extended finger 60EF as is shown in the embodiments of FIG. 3C. The connecting tubing 63, connecting the inflation chamber 60IC can be narrow to only allow the passage of gas 68, while the connecting tubing 36 coupling the two halves of balloon 30 can be larger to allow the passage of water.

As indicated above, the aligner 60 will typically comprise an expandable balloon and for ease of discussion, will now be referred to as aligner balloon 60 or balloon 60. Balloon 60 can be fabricated using materials and methods described above. It has an unexpanded and expanded state (also referred to as a deployed state). In its expanded or deployed state, balloon 60 extends the length of capsule 20 such that forces exerted by the peristaltic contractions of the small intestine SI on capsule 20 serve to align the longitudinal axis 20LA of the capsule 20 in a parallel fashion with the longitudinal axis LAI of the small intestine SI. This in turn serves to align the shafts of tissue penetrating articles 40 in a perpendicular fashion with the surface of the intestinal wall IW to enhance and optimize the penetration of tissue penetrating articles 40 into the intestinal wall IW. In addition to serving to align capsule 20 in the small intestine, aligner 60 is also configured to push delivery mechanism 70 out of capsule 20 prior to inflation of delivery balloon 72 so that the delivery balloon and/or mechanism is not encumbered by the capsule. In use, this push out function of aligner 60 improves the reliability for delivery of the therapeutic agent since it is not necessary to wait for particular portions of the capsule (e.g., those overlying the delivery mechanism) to be degraded before viable cells delivery can occur.

Balloon 60 may be fluidically coupled to one or more components of device 10 including balloons 30 and 72 by means of polymer tube or other fluidic couplings 62 which may include a tube 63 for coupling balloons 60 and 30 and a tube 64 for coupling balloon 60 and balloon 72. Tube 63 is configured to allow balloon 60 to be expanded/inflated by pressure from balloon 30 (e.g., pressure generated the mixture of chemical reactants within balloon 30) and/or otherwise allow the passage of liquid between balloons 30 and 60 to initiate a gas generating chemical reaction for inflation of one or both of balloons 30 and 60. Tube 64 connects balloon 60 to 72 so as to allow for the inflation of balloon 72 by balloon 60. In many embodiments, tube 64 includes or is coupled to a control valve 55 which is configured to open at a selected pressure so as to control the inflation of balloon 72 by balloon 60. Tube 64 may thus comprise a proximal portion 64$p$ connecting to the valve and a distal portion 64$d$ leading from the valve. Typically, proximal and distal portions 64$p$ and 64$d$ will be connected to a valve housing 58 as is described below.

Valve 55 may comprise a triangular or other shaped section 56 of a material 57 which is placed within a chamber 58$c$ of a valve housing 58 (alternately, it may be placed directly within tubing 64). Section 57 is configured to mechanically degrade (e.g., tears, shears, delaminates, etc.) at a selected pressure so as to allow the passage of gas through tube 64 and/or valve chamber 58$c$. Suitable materials 57 for valve 55 can include bees wax or other form of wax and various adhesives known in the medical arts which have a selectable sealing force/burst pressure. Valve fitting 58 will typically comprise a thin cylindrical compartment (made from biodegradable materials) in which section 56 of material 57 is placed (as is shown in the embodiment of FIG. 3B) so as to seal the walls of chamber 58$c$ together or otherwise obstruct passage of fluid through the chamber. The release pressure of valve 55 can be controlled through selection of one or more of the size and shape of section 56 as well as the selection of material 57 (e.g., for properties such as adhesive strength, shear strength etc.). In use, control valve 55 allows for a sequenced inflation of balloon 60 and 72 such that balloon 60 is fully or otherwise substantially inflated before balloon 72 is inflated. This, in turn, allows balloon 60 to push balloon 72 along with the rest of delivery mechanism 70 out of capsule 20 (typically from body portion 20$p'$) before balloon 72 inflates so that deployment of tissue penetrating articles 40 is not obstructed by capsule 20 In use, such an approach improves the reliability of the penetration of tissue penetrating articles 40 into intestinal wall IW both in terms of achieving a desired penetration depth and delivering greater numbers of the penetrating articles 40 contained in capsule 20 since the advancement of the articles into intestinal wall IW is not obstructed by capsule wall 20$w$.

As is describe above, the inflated length 60$l$ of the aligner balloon 60 is sufficient to have the capsule 20 become aligned with the lateral axis of the small intestine from peristaltic contractions of the intestine. Suitable inflated lengths 60$l$ for aligner 60 can include a range between about ½ to two times the length 20$l$ of the capsule 20 before inflation of aligner 60. Suitable shapes for aligner balloon 60 can include various elongated shapes such as a hotdog like shape. In specific embodiments, balloon 60 can include a first section 60' and a second section 60", where expansion of first section 60' is configured to advance delivery mechanism 70 out of capsule 20 (typically out of and second section 60" is used to inflate delivery balloon 72. In these and related embodiments, first and second sections 60' and 60" can be configured to have a telescope-style inflation where first section 60' inflates first to push mechanism 70 out of the capsule (typically from body portion 20$p'$) and second section 60" inflates to inflate delivery member 72. This can be achieved by configuring first section 60' to have smaller diameter and volume than second section 60" such that first section 60' inflates first (because of its smaller volume) and with second section 60" not inflating until first section 60' has substantially inflated. In one embodiment, this can be facilitated by use of a control valve 55 (described above) connecting sections 60' and 60" which does not allow passage of gas into section 60" until a minimum pressure has been reached in section 60'. In some embodiments, the aligner balloon can contain the chemical reactants which react upon mixture with water or other liquid from the deploying balloon.

In many embodiments, the deployment member 30 will comprise an expandable balloon, known as the deployment balloon 30. In various embodiments, deployment balloon 30 is configured to facilitate deployment/expansion of aligner balloon 60 by use of a gas, for example, generation of a gas 69 from a chemical. The gas may be generated by the reaction of solid chemical reactants 65, such as an acid 66 (e.g., citric acid) and a base 67 (e.g., potassium bicarbonate, sodium bicarbonate and the like) which are then mixed with water or other aqueous liquid 68. The amount of reactants may be chosen using stoichiometric methods to produce a selected pressure in one or more of balloons 30, 60 and 72. The reactants 65 and liquids can be stored separately in balloon 30 and 60 and then brought together in response to a trigger event, such as the pH conditions in the small intestine. The reactants 65 and liquids 68 can be stored in either balloon, however in preferred embodiments, liquid 68 is stored in balloon 30 and reactants 65 in balloon 60. To allow for passage of the liquid 68 to start the reaction and/or the resulting gas 69, balloon 30 may be coupled to aligner balloon 60 by means of a connector tube 63 which also typically includes a separation means 50 such as a degradable valve 50 described below. For embodiments where balloon 30 contains the liquid, tube 63 has sufficient diameter to allow for the passage of sufficient water from balloon 30 to balloon 60 to produce the desired amount of gas to inflate balloon 60 as well inflate balloon 72. Also when balloon 30 contains the liquid, one or both of balloon 30 and tube 63 are configured to allow for the passage of liquid to balloon 60 by one or more of the following: i) the compressive forced applied to balloon 30 by peristaltic contractions of the small intestine on the exposed balloon 30; and ii) wicking of liquid through tube 63 by capillary action.

Figures 6A, 6B:
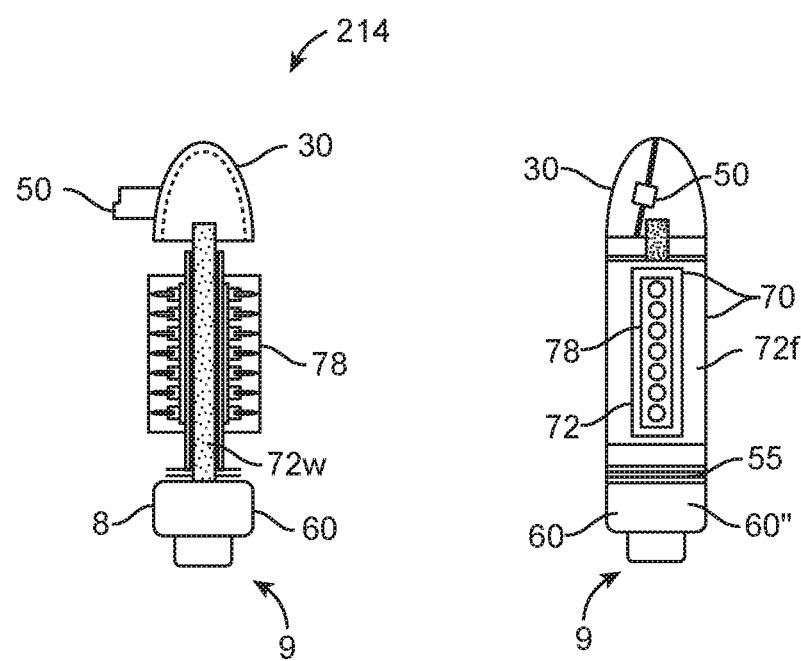
FIGS. 6A and 6B are orthogonal views illustrating embodiments of the final folded multi balloon assembly with the attached delivery assembly.
Figures 7A, 7B:
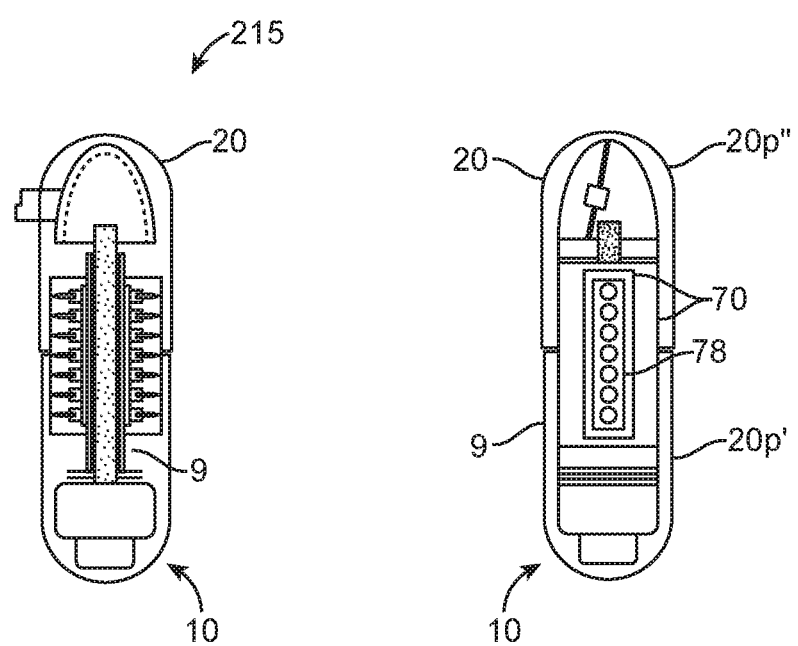
FIGS. 7A and 7B are orthogonal transparent views illustrating embodiments of the final folded multi balloon assembly inserted into the capsule.

Tube 63 will typically include a degradable separation valve or other separation means 50 which separates the contents of balloon 30, (e.g., water 58) from those of balloon 60 (e.g., reactants 65) until the valve degrades. Valve 50 can be fabricated from a material such as maltose, which is degradable by liquid water so that the valve opens upon exposure to water along with the various liquids in the digestive tract. It may also be made from materials that are degradable responsive to the higher pH's found in the intestinal fluids such as methacrylate based coatings. The valve is desirably positioned at location on tube 63 which protrudes above balloon 30 and/or is otherwise sufficient exposed such that when cap 20$p'$ degrades the valve 50 is exposed to the intestinal liquids which enter the capsule. In various embodiments, valve 50 can be positioned to lie on the surface of balloon 30 or even protrude above it (as is shown in the embodiments of FIGS. 6A and 6B), so that is has clear exposure to intestinal fluids once cap 20$p'$ degrades. Various embodiments of the invention provide a number of structures for a separation valve 50, for example, a beam like structure (where the valve comprises a beam that presses down on tube 63 and/or connecting section 36), or collar type structure (where the valve comprises a collar lying over tube 63 and/or connecting section 36). Still other valve structures are also contemplated.

Balloon 30 has a deployed and a non-deployed state. In the deployed state, the deployment balloon 30 can have a dome shape 30$d$ which corresponds to the shape of an end of the capsule. Other shapes 30$s$ for the deployed balloon 30 are also contemplated, such as spherical, tube-shape, etc. The reactants 65 will typically include at least two reactants 66 and 67, for example, an acid such as citric acid and a base such as sodium bicarbonate, which can have about a 1:2 ratio. Other reactants 65 including other acids, e.g., ascetic acid and bases, e.g., sodium hydroxide are also contemplated. When the valve or other separation means 50 opens, the reactants mix in the liquid and produce a gas such as carbon dioxide which expands the aligner balloon 60 or other expandable member.

In an alternative embodiment shown in FIG. 3B, the deployment balloon 30 can actually comprise a first and second balloon 30' and 30" connected by a tube 36 or other connection means 36 (e.g., a connecting section). Connecting tube 36 will typically include a separation valve 50 that is degradable by a liquid as described above and/or a liquid having a particular pH such as basic pH found in the small intestine (e.g., 5.5 or 6.5). The two balloons 30' and 30" can each have a half dome shape 30$hs$ allowing them to fit into the end portion of the capsule when in the expanded state. One balloon can contain the chemical reactant(s) 65 (e.g., sodium bicarbonate, citric acid, etc.) the other the liquid water 68, so that when the valve is degraded the two components mix to form a gas which inflates one or both balloons 30' and 30" and in turn, the aligner balloon 60.

Figure 4A:
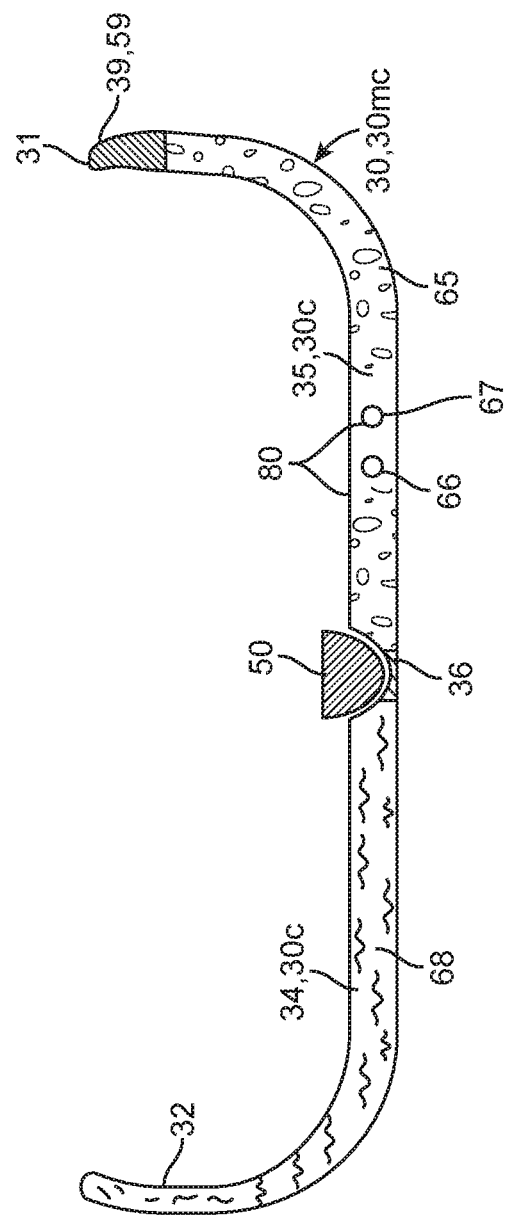
FIGS. 4A-4C are lateral views illustrating embodiments of a multi compartment deployment balloon.
Figure 4B:
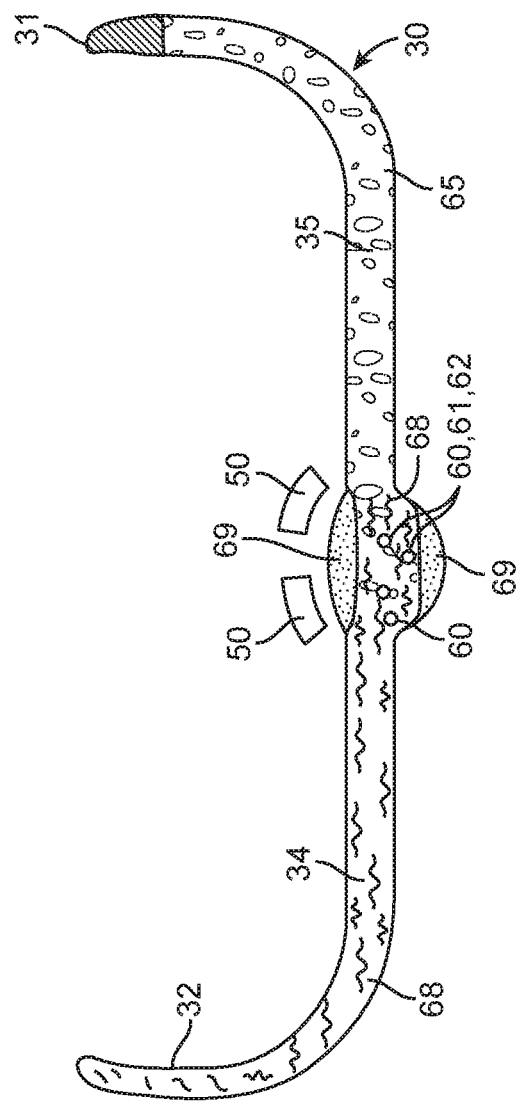
Figure 4C:
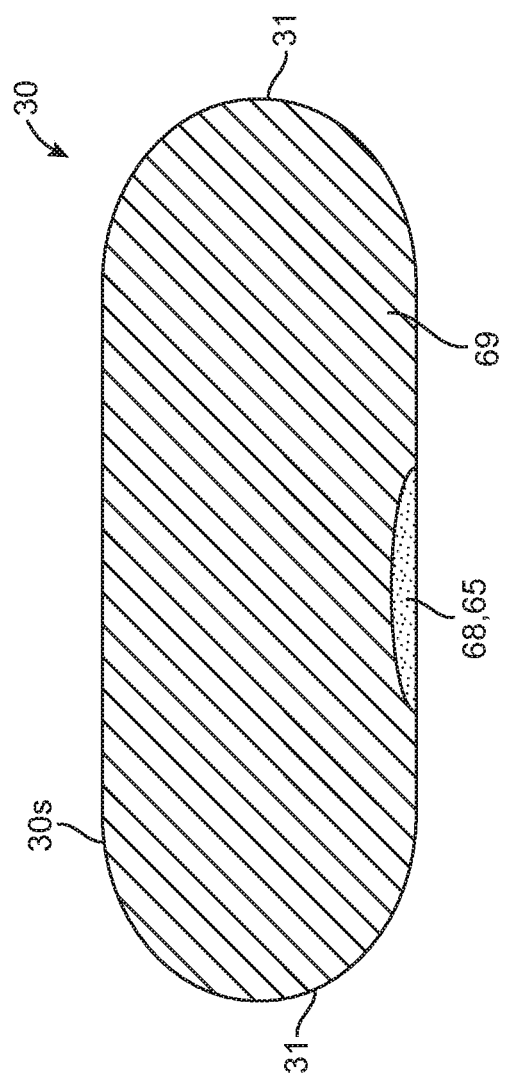

In yet another alternative embodiment, balloon 30 can comprise a multi-compartment balloon 30$mc$, that is formed or other constructed to have multiple compartments 30$c$. Typically, compartments 30$c$ will include at least a first and a second compartment 34 and 35 which are separated by a separation valve 50 or other separation means 50 as is shown in the embodiment of FIG. 4A. In many embodiments, compartments 34 and 35 will have at least a small connecting section 36 between them which is where separation valve 50 will typically be placed. A liquid 68, typically water, can be disposed within first compartment 34 and one or more reactants 65 disposed in second compartment 35 (which typically are solid though liquid may also be used) as is shown in the embodiment of FIG. 4A. When valve 50 opens (e.g., from degradation caused by fluids within the small intestine) liquid 68 enters compartment 35 (or vice versa or both), the reactant(s) 65 mix with the liquid and produce a gas 69 such as carbon dioxide which expands balloon 30 which in turn can be used to expand one or more of balloons 60 and 72.

Reactants 65 will typically include at least a first and a second reactant, 66 and 67 for example, an acid such as citric acid and a base such as sodium bi-carbonate or potassium bi-carbonate. As discussed herein, in various embodiments they may be placed in one or more of balloon 30 (including compartments 34 and 35 or halves 30' and 30") and balloon 60. Additional reactants, including other combinations of acids and bases which produce an inert gas by product are also contemplated. For embodiments using citric acid and sodium or carbonate, the ratios between the two reactants (citric acid to potassium bicarbonate) can be in the range of about 1:1 to about 1:4, with a specific ratio of about 1:3. Desirably, solid reactants 65 have little or no absorbed water. Accordingly, one or more of the reactants, such as sodium bicarbonate or potassium bicarbonate can be pre-dried (e.g., by vacuum drying) before being placed within balloon 30. Other reactants 65 including other acids, e.g., ascetic acid and bases are also contemplated. The amounts of particular reactants 65, including combinations of reactants can be selected to produce particular pressures using known stoichiometric equations for the particular chemical reactions as well as the inflated volume of the balloon and the ideal gas law (e.g., $PV=nRT$). In particular embodiments, the amounts of reactants can be selected to produce a pressure selected one or more of balloons 30, 60 and 72 to i) achieve a particular penetration depth into the intestinal wall; ii) and produce a particular diameter for one or more of balloons 30, 60 and 72; and iii) exert a selected amount of force against intestinal wall IW. In particular embodiments, the amount and ratios of the reactants (e.g., citric acid and potassium bicarbonate) can be selected to achieve pressures in one or more of the balloons 30, 60 and 72 in the range of 10 to 15 psi, with smaller and larger pressures contemplated. Again the amounts and ratios of the reactants to achieve these pressures can be determined using known stoichiometric equations.

In various embodiments of the invention using chemical reactants 65 to generate gas 69, the chemical reactants alone or in combination with the deployment balloon 30 can comprise a deployment engine for 80 deploying one or both of the aligner balloon 60 and delivery mechanism 70 including delivery balloon 72. Deployment engine 80 may also include embodiments using two deployment balloons 30 and 30" (a dual dome configuration as shown in FIG. 3B), or a multi compartment balloon 30$mc$ as shown in FIG. 4A. Other forms of a deployment engine 80 are also contemplated by various embodiments of the invention such as use of expandable piezo-electric materials (that expand by application of a voltage), springs and other shape memory materials and various thermally expandable materials.

One or more of the expandable balloons 30, 60 and 72 will also typically include a deflation valve 59 which serves to deflate the balloon after inflation. Deflation valve 59 can comprise biodegradable materials which are configured to degrade upon exposure to the fluids in the small intestine and/or liquid in one of the compartments of the balloon so as to create an opening or channel for escape of gas within a particular balloon. Desirably, deflation valves 59 are configured to degrade at a slower rate than valve 50 to allow sufficient time for inflation of balloons, 30, 60 and 72 before the deflation valve degrades. In various embodiments, of a compartmentalized balloon 30, deflation valve 59 can correspond to a degradable section 39 positioned on an end portion 31 of the balloon as is shown in the embodiment of FIG. 4A. In this and related embodiments, when degradable section 39 degrades from exposure to the liquid, balloon wall 32 tears or otherwise comes apart providing for a high assurance of rapid deflation. Multiple degradable sections 39 can be placed at various locations within balloon wall 32.

In various embodiments of balloon 72, deflation valve 59 can correspond to a tube valve 73 attached to the end 72e of the delivery balloon 72 (opposite to the end which is coupled to the aligner balloon) as is shown in the embodiment of FIG. 3B. The tube valve 73 comprises a hollow tube 73t having a lumen that is obstructed at a selected location 73l with a material 73m such as maltose that degrades upon exposure to fluid such as the fluid in the small intestine. The location 73l of the obstructing material 73m in tube 73t is selected to provide sufficient time for the delivery balloon 72 to inflate and deliver the tissue penetrating articles 40 into the intestinal wall IW before the obstructing material dissolves to open valve 73. Typically, this will be close to the end 73e of the tube 73t, but not quite so as to allow time for liquid to have to wick into the tube lumen before it reaches material 73m. According to one or more embodiments, once the deflation valve 73 opens, it not only serves to deflate the delivery balloon 72 but also the aligner balloon 60 and deployment balloon 30 since in many embodiments, all three are fluidically connected (aligner balloon being fluidically connected to delivery balloon 72 and the deployment balloon 30 being fluidically connected to aligner balloon 60). Opening of the deflation valve 73 can be facilitated by placing it on the end 72e of the delivery balloon 72 that is forced out of capsule 20 by inflation of the aligner balloon 60 so that the deflation valve has good exposure to liquids in the small intestine. Similar tube deflation valves 73 can also be positioned on one or both of aligner balloon 62 and the deployment balloon 30. In these later two cases, the obstructing material in the tube valve can be configured to degrade over a time period to allow sufficient time for inflation of delivery balloon 72 and advancement of tissue penetrating articles 40 into the intestinal wall.

Additionally, as further backup for insured deflation, one or more puncture elements 82 (shown in FIG. 2A) can be attached to the inside surface 24 of the capsule such that when a balloon (e.g., balloon 30, 60, 72) fully inflates it contacts and is punctured by the puncture element 82. Puncture elements 82 can comprise short protrusions from surface 24 having a pointed tip. In another alternative or additional embodiment of a means for balloon deflation, one or more of the tissue penetrating articles 40 can be directly coupled to the wall of 72w of balloon 72 and configured to tear away from the balloon when they detach, tearing the balloon wall in the process.

Figure 8A:
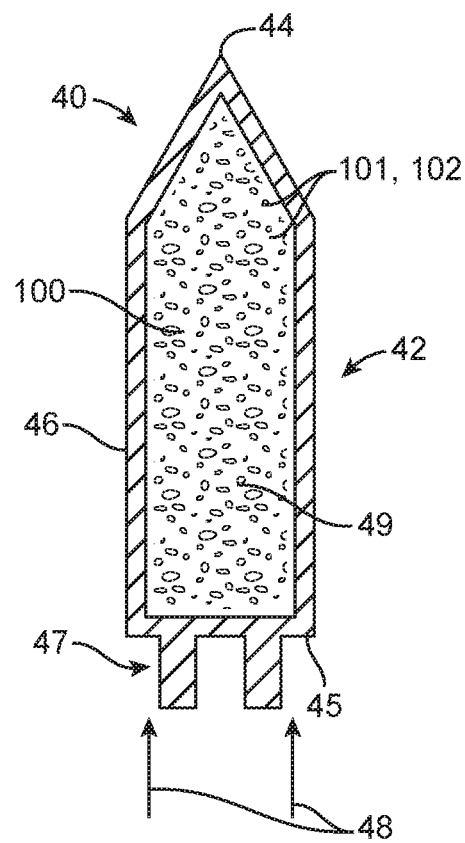
FIG. 8A is a cross-sectional view of an embodiment of a tissue penetrating article constructed in accordance with the principles of the present invention.
Figure 8B:
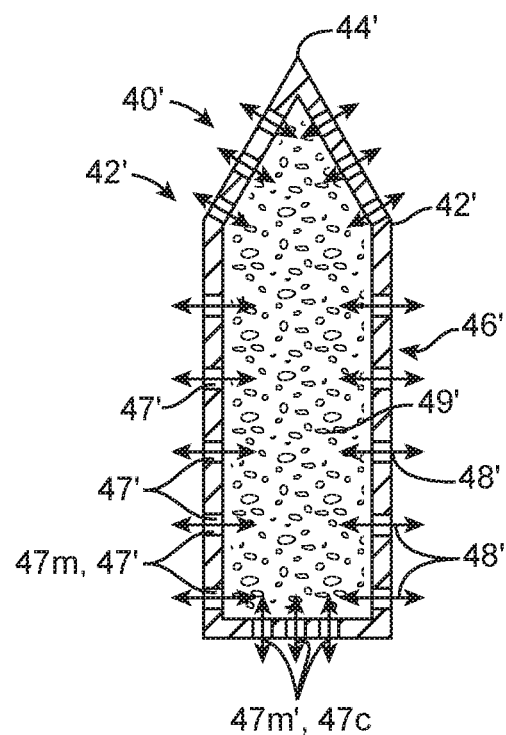
FIG. 8B is a cross-sectional view of an alternative embodiment of a tissue penetrating article constructed in accordance with the principles of the present invention.

With specific reference to the inventions claimed herein, tissue penetrating articles (TPA) 40 and 40' are illustrated in FIGS. 8A and 8B. A first exemplary TPA 40 (FIG. 8A) includes a shell 42 having a tissue-penetrating distal tip 44 and a proximal base 45. The tissue-penetrating distal tip 44 may comprise a generally conical structure, as illustrated, with a pointed tip that can penetrate into tissue when a propulsive force is applied to the proximal base 45 in a direction toward the tip (as indicated by arrows 48). Optionally, a coupling structure 47 will be provided on the end surface of the base to engage the TPA with the propulsion capsules described herein. The shell can be fabricated by one or more of molding, machining, dip-casting and other polymer fabrications methods known in the art. Further according to specific embodiments, the shells including embodiments having fenestrations described below can be fabricated using various 3D-printing methods known in the art. Use of 3-Printing provides the benefit of increased accuracy and precision of the dimensions of the TPA along with reduced contamination, fabrication time and cost.

In the embodiment of FIG. 8A, the shell or barrier 42 will have a generally impermeable wall 46 which biodegrades over time in a tissue environment, such as an intestinal tissue environment, typically within the exemplary time periods set forth earlier in this application. According to various embodiments, the biodegradable shell 42 may be formed from a biodegradable metal, such as magnesium, iron, zinc, or the like, or from a biodegradable polymer, such as poly lactic acid (PLA), poly(lactic-co-glycolic acid) (PLGA), or the like. In all cases, the biodegradable shell will have sufficient durability (e.g. in terms of structural integrity) so that the shell remains intact to protect the viable cells (e.g. dose 102 of cell preparation 100 containing a cell type 101) being delivered until the article has been implanted in a target tissue site in the GI tract or other location. The time it takes from introduction to the patient until the shell erodes sufficiently to expose and/or release the viable cells can be selected based on various factors including the particular materials and construction of the shell. In one or more embodiments, the biodegradation time can be programmed or otherwise controlled by selection of one or more of the following: i) shell material selection (e.g., particular bioerodable polymers); ii) shell wall thickness; iii) the inclusion pits or other erosion initiation sites on the shell surface so as to provide sacrificial layers over the shell, or the like Embodiments of the invention are useful for orally delivering a variety of cells in viable condition to a human patient or other mammalian animal. The viable cells can include those used for both therapeutic and diagnostic purposes. For example, the cells can include those which produce therapeutic agents such as insulin or various incretins, stem cells which differentiate into selected cells or cells for seeding or reseeding a selected tissue site such as the mucosa at one or more locations in the GI tract. Embodiments of the invention are be particularly useful for delivering viable pancreatic beta cells or other pancreatic entero-endocrine cells to the patient's digestive organ or intestinal tissue so that the cells can produce insulin for the treatment of diabetes or other glucose control conditions. Such pancreatic enter-endocrine cells can be delivered to the pancreas or in some cases to the small intestine where the cells are seeded and become incorporated into the intestinal wall so as to release insulin into the blood stream from the small intestine.

Embodiments of the invention are not limited however, to the delivery of beta cells, but rather can be used to deliver a variety of other viable cell masses to a patient for the treatment of a variety of conditions as well as for diagnostic purposes. Other exemplary viable cells to be delivered include without limitation, human and other stem cells, specifically including mesenchymal stem cells and hematopoietic stem cells; Gastric entero-endocrine cells such as G-cells; or Intestinal enter-endocrine cells such as L-cells K-cells, I-cells, N-cells and S-cells. They may also various mucosal cells, including gastro-intestinal mucosal cells for purposes of reseeding the mucosal lining of the stomach or small intestine; and differentiated cells, including those of the immune system including lymphocytes such as T-cells, B-cells and Killer cells; and Granulocytes such as neutrophils eosinophils and monocytes, and the like.

In other embodiments, the invention provides methods whereby the patient takes swallowable articles containing viable cells to reseed selected portions of the GI tract with cells such as hormone or other peptide producing cells that produce a therapeutic effect. For example according to one or more embodiments the invention provides methods whereby the small intestine or other location in the GI tract are reseeded with L-cells or K-cells to produce incretin or G-cells to produce Gastrin. In specific embodiments, the cells can comprise various mucosal cells to reseed the mucosa of the stomach, pylorus and duodenum for example to treat one or more of a gastric, pyloric or duodenal ulcer or loss of such cells due to cancer or chemotherapeutic treatment thereof. Further, the articles can be configured to reseed specific portions of specific GI organs such as the duodenum or jejunum of the small intestine and the pyloric region of the stomach. The articles can be configured to inject cells into theses specific regions by the use of pH sensitive coatings described herein such as various EUDRAGIT coatings and others known in the art which degrade in response to specific pH's in specific location, such as more acid pH in the stomach (1.5-3.5) and increasingly less acidic pH in the small intestine (5.5 in the duodenum and 6.5-6.8 in the jejunum).

According to one or more embodiments, the cells to be delivered are desirably maintained within a protected interior of the TPA suspended in a viability-sustaining gel 49. Such gels are well known in the art and described in the medical and patent literature. A suitable gel may comprise a gelatin, typically at a weight percentage that ranges from about 4 to about 20 weight %, usually between about 5-10 weight % of the total weight of the gel (similar volume percentages may also be considered. In various embodiments, the gelatin may be replaced or supplemented with one or more of collagen, fibrin, fibrinogen, albumin, and keratin and/or other glutamine/lysine rich peptides at concentrations which foster cell viability. In various embodiments gels 49 may be injected into the shells, may be a precast gel (e.g., put in place before the shell is completely formed), or may be provided as beads or micelles. The gel will typically be a hydrogel and in many embodiment, may be frozen or chilled within the shell prior to use. The hydrogel will usually be consumed over time by the cells being supported by the gel, but such consumption will be held in abeyance by freezing and/or reduced by maintaining the cells at chilled temperatures (e.g. 33 to 45° F., though other temperature ranges are also contemplated).

In other embodiments, the gel may correspond to a protein-based hydrogel with a crosslinking agent that is mixed in with the gel. Also, in particular embodiments, the gel may contain oxygen (by being partially or fully saturated with the gas) prior to filling or after filling in the shell to further enhance the viability sustaining properties of the gel. In other embodiments, the gel may contain nitrogen or other inert gas so as to enhance preservation of the cells prior to use. In related embodiments, the gel can contain both oxygen and nitrogen or other inert gas. The particular amount of saturation of such gases can be selected based upon one or more of the intended shelf life of the swallowable capsule containing the viable cells and the storage conditions (e.g., whether the capsule 10 or TPA 40 is stored at room temperature, refrigerated below room temperature or frozen). According to various embodiments the saturation level of oxygen in the gel can range from about 5 to 100%, with specific embodiments of 10, 20, 25, 30, 40, 50, 60, 70, 80, 90 and 95%). The saturation level for nitrogen or other inert gas in the gel can have similar values.

According to particular embodiments, the hydrogel may correspond to a transglutaminase that is reactive with fibrin, fibrinogen, collagen, albumen, involucrin, or gelatin. Protein gels can be combined with glycosaminoglycan (GAG) or proteoglycans such as, but no limited to hyaluronic acid, chondroitin sulfate, heparin, and keratin sulfate. Protein gels can also be combined with polysaccharides, such as, but not limited to starch, cellulose, methylcellulose, alginate, agarose, chitin or chitosan, glycogen, xanthan gum, dextran, welan gum, gellan gum, diutan gum, and pullulan. Protein gels can be also combined with fatty substance such as, but not limited to lecithin. Protein gels can be also combined with synthetic polymers such as, but not limited to PEG (polyethylene glycol). See for example, US Patent Publication No. 2010/0215715 (the full disclosure of which is incorporated herein by reference for all purposes) for further explanation of how this may be done.

As discussed herein in many embodiments, the invention provides methods for delivery of viable cells into solid tissue of a patient such as that in the gastro intestinal tract, wherein the cells are put into a reversible suspended state of animation prior to being administered to the patient including prior to being put into the article wherein they reanimate after being delivered to the patient so as to produce a desired therapeutic effect. Such therapeutic effects can include example, producing one or more therapeutic compounds (e.g., insulin, integrin, etc.). Suspended animation also includes states of slowed cellular animation wherein the cellular metabolism and processes are significantly slowed. Typically the cells will be put into the state of suspended or slowed state of animation by freezing or chilling the cells and/or the gel containing them within the article prior to administering the article to the patient. Chilling may be done to a temperature in the range of 50 to 33° F. with a preferred range of 39 to 40° F. In an alternative or variation, the cells and/or gel containing them may be frozen or chilled prior to being placed into the article. Freezing the articles and the cells therein prior to administration is particularly useful as it can preserve the cells for extended periods of time in a reversible state of suspended animation without the need to supply nutrients and remove cellular products. Similar results can be achieved by chilling the cells as well. Once the articles are administered to the patient, however, the cells will thaw and warm within a short time period to become reanimated and resume cellular processes. For certain cells, reanimation of the cells results in the cells resuming production of various therapeutic by-products depending upon the cell (e.g. insulin, incretin, gastrin, etc.). Depending upon the cell and the particular type of suspended animation process (freezing, chilling, freeze drying etc.), reanimation can be further facilitated or may initially occur by insertion of the cells into the patient's tissue such as the wall of the small intestine so as to provide them access to blood supply bringing them nutrients and carrying away waste products. Other methods of producing suspended reversible animation of the viable cells are also contemplated besides freezing and chilling. These may include for example, use of certain compounds in the gel and/or charging the gel with an inert gas (e.g., nitrogen) and lyophilizing of the cells (or other freeze drying methods) prior to administration. In the case of lyophilizing or other freeze drying method, re-animation can be brought about by insertion of the cells into or brought in contact with the patient's solid tissue (e.g. such as into the walls of the small intestine or other location in the intestinal tract) where the cells are warmed, rehydrated by the patient's interstitial fluids and exposed to the patient's blood supply to bring the cells nutrient's and carry away waste products (e.g. $CO_2$, etc.). Embodiments of the invention contemplate a number of different cell types that can be lyophilized so as to be put into a reversible state of suspended animation including for example, stem cells, mesenchymal stem cells, L-cells, K-cells, G-cells, Beta-Cells and the like. Specific description of methodology for lyophilization of stem cells and other cell types may be found in a paper by Zhang, et al, entitled, "Preliminary study on the freeze-drying of human bone marrow-derived mesenchymal stem cells" J Zhejiang Univ Sci B. 2010 November; 11(11): 889-894 which is incorporated herein for all purposes. Once the cells are kept put into the reversible suspended state of animation, they may be kept in that state during oral delivery by enclosed by various embodiments of the tissue penetrating article described herein. The article can be configured to protect the cells from various body fluids, particularly those in gastrointestinal tract which may lyse or otherwise damage the cells or bring them out of their state of suspended animation before they can be delivered to their intended target tissue site (e.g., into the walls of the small intestine). Once the article is inserted into the target tissue site, it can be configured to biodegrade as described herein so as to bring the cells into contact with body fluids (e.g., blood, interstitial fluid, etc.) which reanimate the cells bringing them out of their state of suspended animation. In the case of frozen or chilled cells, the article can also be configured to provide a degree of thermal insulation including during oral delivery to prevent or slow unwanted reanimation of the cells from thawing and/or rewarming. In alternative or additional embodiments, the article can be configured to be degrade or otherwise be broken down to release their payload of cells by the external delivery (e.g. outside the body) of energy such as RF or acoustical energy (e.g., using RF electrodes or piezo electric crystals for ultrasonic or other acoustical energy). In this way the patient or medical provider can release the cells to the intended delivery site on demand.

For orally delivered frozen or otherwise suspended cells, once the cells are reanimated (e.g. by the patient's body heat) they may be at risk of degradation during oral delivery from the gastrointestinal environment. Accordingly, in various embodiments of the shell described herein can be configured to protect the now metabolically active cells as they pass through a patient's gastrointestinal tract where they would be exposed to the digestive conditions of the stomach which, without protection, would quickly kill the cells. Once penetrated into the intestinal tract, the article will be implanted into the intestinal tissue, thus releasing the viable cells where they are now in an environment in which cell viability can be maintained and they can generate the useful therapeutic substances which they produce. Embodiments of these methods employ articles which may have the preferred characteristics and dimensions discussed above in connection with articles of the present invention.

FIG. 8B illustrates an alternative embodiment of a TPA 40' including a shell or barrier 42' and a tissue-penetrating distal tip 44". In contrast to the TPA 40, TPA 40' has a shell wall 46' that has fenestrations 47', i.e. small holes or apertures, which are sized to allow exchange of fluids (indicated by arrows 48') and molecules (such as those produced by viable cells 101) with the tissue embodiment but which retain and protect the cells and the supporting gels 49' within the interior of the shell. When the shell 42' has such fenestrations 47', it will not always be necessary that the shell wall 46' be fully or even partially biodegradable since the cells can receive oxygen and nutrients from the surrounding tissue which diffuse in through the fenestrations and release therapeutically useful metabolites and other cellular products (e.g. insulin, integrins, Gastrin, etc.) into the tissue by diffusion out through the fenestrations. Usually, however, it will be preferable that even the fenestrated walls be biodegradable over a selected time period (e.g. days, weeks, months etc.). The fenestrations can be produced by various methods known in the polymer and other material science arts including, for example, solvent methods (e.g., solvent dissolution), laser drilling, and 3-D printing methods known in the art.

In various embodiments, the fenestrations 47' can have a diameter correlated to a major diameter or other major dimension of the particular cell or cells contained within the article. In particular embodiments the fenestrations diameter can be matched to a selected percentage (e.g., 1, 5, 10, 25, 50% etc.) of the major cell dimension. The fenestrations 47' will typically have a width in the range from about 0.1 to 15 µm more preferably about 0.5 to 5 µm and/or an area in the range from 0.03 to 707 µm$^2$, more preferably about 0.79 to 79 µm$^2$. According so some embodiments, when the shell comprises fenestrations, it may be formed from a non-biodegradable material since many cells can maintain viability through fluid and substance exchange with the implanted tissue and can release therapeutically useful cell products to the tissue through the same fenestrations. Usually, however, even with fenestrations, it will be preferable to form the shell wall 46' from the biodegradable material. In alternative or additional embodiment, the fenestrations may be configured to produce a distinct acoustical signature or pattern when pinged by an external acoustical transceiver such as an ultrasound transceiver or other piezo electric based acoustical transceiver and thus function as markers 47m (e.g., echogenic markers) when imaged ultrasonically or by other acoustical imaging modality or sensing modality. Further as the fenestrations break down due to bio-erosion of the article, the acoustical signature of shell in response to an acoustical ping changes such the degree of bio-erosion of the shell can be discerned. In particular embodiments the fenestrations can be configured to produce distinct acoustical patterns when there is no bio-erosion, and when there is 25, 50 and 75% bio-erosion etc. and thus provide indicia 47i of the degree of degradation of the shell. In this way, the fenestrations provide actionable information for the user to know when the article/shell has degraded sufficiently to release the cells to the selected tissue site. The specific acoustical signatures can be produced by the size and spacing of the fenestrations so to produce a specific acoustical reflective pattern. In specific embodiments this can be achieved by correlating one or both of the fenestration diameter or spacing to wavelength of the particular acoustical signal used to ping the fenestration. In alternative or additional embodiments for providing information on the state of degradation of the articles, the articles can include other acoustical markers 47m' or indicia 47c configured to provide specific acoustical signatures of the percent degradation of the article.

Figure 8C:
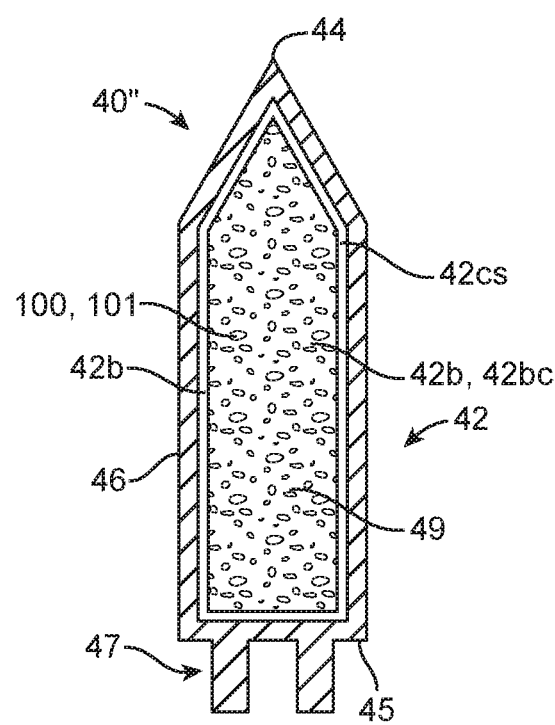
FIG. 8C is a cross-sectional view of a yet another alternative embodiment of a tissue penetrating article constructed in accordance with the principles of the present invention which includes a moisture barrier on an inner surface of the article.

Referring now to FIG. 8C, in another embodiment of a TPA, indicated as 40" (with the other common element numbers staying the same as FIG. 8A for ease of writing), the TPA can including a moisture barrier 42b on an interior surface 42cs of the shell 42. The moisture barrier is configured to slow or prevent degradation of shell 42 and shell wall 46 from any moisture from preparation 100 including from gel 49. In use the barrier 42b serves to improve the shelf life of the shell 42 and TPA 40" by preventing such degradation. Once the shell wall 42 degrades from the outside such the barrier 42b is no longer fully mechanically supported by wall 46, the barrier is configured to shear or otherwise mechanically fail due to forces imparted on the coating from tissue within the body (e.g. from peristaltic contraction, breathing, blood flow organ movement etc.). This can be achieved through the choice of material for the barrier and its thickness, for example thickness of the barrier 42b can range from about 0.01 to 0.001". Thinner coatings being more susceptible to shearing from internal body forces and/or from forces resulting from degradation of the shell 42 (e.g. when pieces of the shell come off). In preferred embodiments, the barrier 42b comprises a coating 42bc including various water impermeable polymer coatings known in the art. Coating 42bc may applied using various spray, dip coating and plasma deposition methods known in the art. In one embodiment coating 42bc may comprise a butyl rubber known in the medical material arts.

Figure 8D:
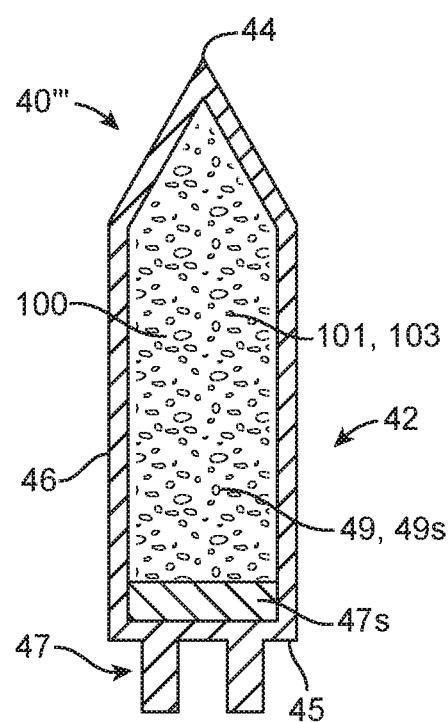
FIG. 8D is a cross-sectional view of a yet another alternative embodiment of a tissue penetrating article constructed in accordance with the principles of the present invention which includes a shock absorbing structure in an interior of the article and/or a shock absorbing gel configured to reduce forces imparted onto the viable cells.

Referring now to FIG. 8D, in another embodiment of the TPA indicate as TPA as TPA ''' (all other element number staying the same), article 40''' can include an shock absorbing structure 47s positioned on a bottom interior surface of the shell wall 46 (the bottom surface being at the opposite end from distal tip 44). Shock absorbing structure 47s may comprise various biodegradable elastomers known in the art and is configured to absorb and reduce the force imparted from bottom surface 45 to preparation 100 including cells 101 when a propulsion force is imparted to the bottom surface to propel the article 40''' into tissue. The imparted force is desirably reduced sufficiently to reduce or prevent any damage or injury to cells 101, 103 in preparation 100. In various embodiments the shock absorber 47s can be configured to reduce the force transmitted to preparation 100 cells 101 to less than 0.2 lbs more preferably less than 0.1 lbs and still more preferably less than 0.05 lbs. Such force reductions can be obtained by selection of the thickness and durometer of the shock absorber 47s. In related embodiments the viscoelastic properties of gel 49 can be selected such that the gel acts as a shock absorbing medium 49s to reduce the aforementioned forces imparted to cells 101 from article propulsion as described above. Suitable viscoelastic properties of the gel which can be selected to achieve force reduction can include one or more of viscosity and storage modulus (G). In particular embodiments the viscosity of the gel can range from about 1 to 20 times that of water and the storage modulus can range from about 200 to 1000 Pascals (over a range of deformations) more preferably form about 200 to 800 Pascals and still more preferably about 200 to 600 Pascals.

For embodiments of the invention where the viable cells are frozen, the TPA 40 can be modified to accommodate such freezing. For example, the space within the interior space within TPA for the cell containing gel 49 can be increased so as to provide for expansion of the frozen gel without damage to the TPA including structural damage such as cracks disrupting the barrier function of barrier or wall 46'. In either approach, the amount of volumetric empty space of interior of TPA after filling with gel 49 can ranch from about 5, to about 90% with specific embodiments of 7.5, 10, 20, 30, 40, 50 and 75%. In a preferred embodiment the amount of volumetric empty space of the interior of the TPA 40 may correspond to the amount of volumetric expansion of water upon freezing which ranges from about 9 to about 10%.

Also, the TPA including barrier or wall 46' can be fabricated from materials which are resistant to structural damage from freezing such as cracking, crazing etc which may compromise the barrier function of wall 46'. Such resistant materials may comprise various low temperature tolerant biocompatible polymers known in the polymer and biomedical materials arts.

A description will be provided of delivery mechanism 70. Typically, the mechanism will comprise a delivery assembly 78 (containing tissue penetrating articles 40) that is attached to delivery balloon 72 as is shown in the embodiment of FIGS. 6A and 6B. Inflation of the delivery balloon provides a mechanical force for engaging delivery assembly 72 outwards from the capsule and into the intestinal wall IW so as to insert tissue penetrating articles 40 into the wall. In various embodiments, the delivery balloon 72 can have an elongated shape with two relatively flat faces 72f connected by an articulated accordion-like body 72b. The flat faces 72f can be configured to press against the intestinal wall (IW) upon expansion of the balloon 72 so as to insert the tissue penetrating articles (TPAs) 40 into the intestinal wall. TPAs 40 (either by themselves or as part of a delivery assembly 78 described below) can be positioned on one or both faces 72f of balloon 70 to allow insertion of viable cells containing TPAs 40 on opposite sides of the intestinal wall. The faces 72f of balloon 72 may have sufficient surface area to allow for placement of a number of viable cells containing TPAs 40 on each face.

Figure 9:
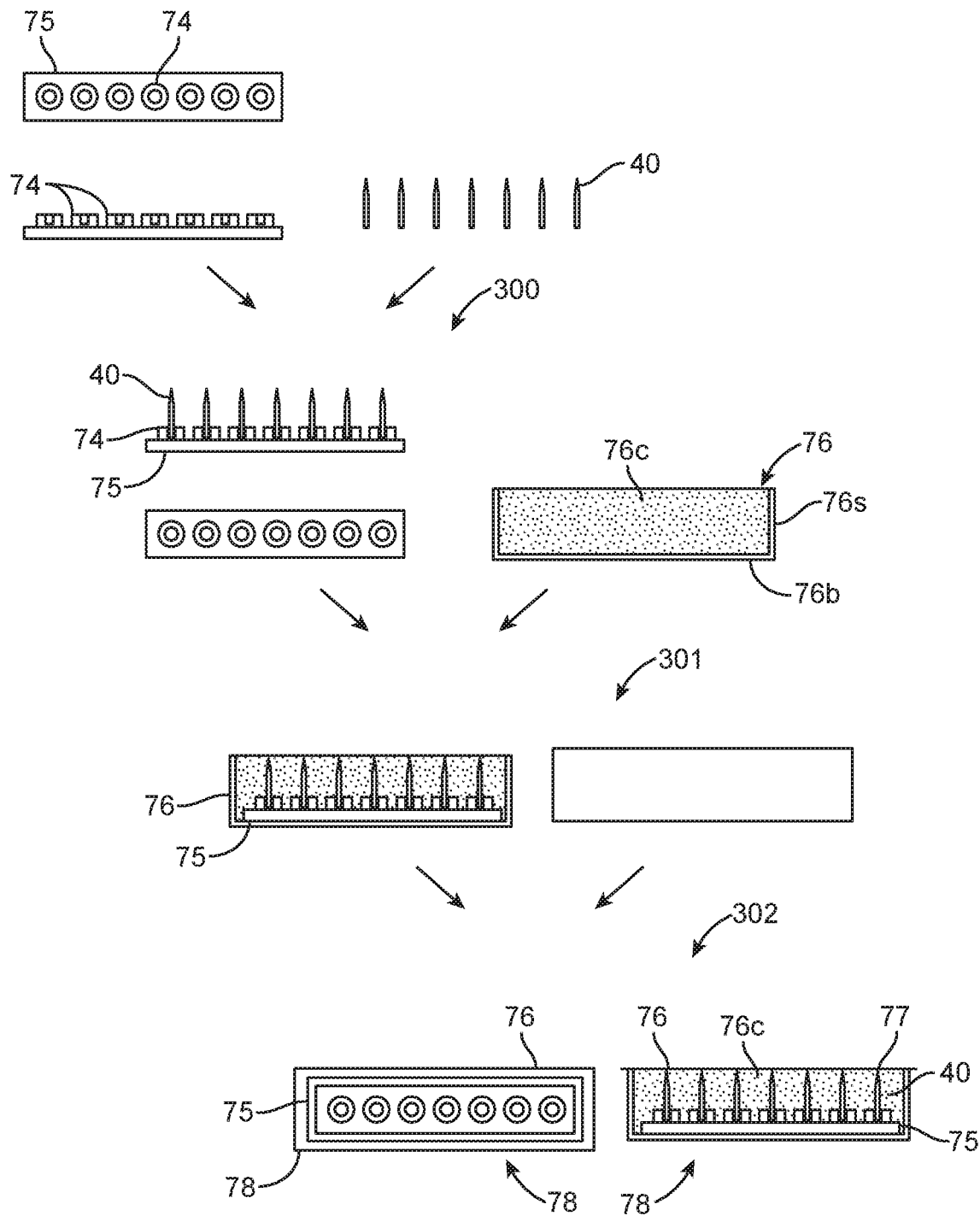
FIG. 9 provides assorted views of the components and steps used to assemble an embodiment of the delivery assembly.

Referring now to FIG. 9, a description will now be provided of assembly of delivery assembly 78. In a first step 300, one or more tissue penetrating articles 40 can be detachably coupled to a biodegradable advancement structure 75 which may correspond to a support platform 75 (also known as platform 75). In preferred embodiments, platform 75 includes one or more openings 74 for insertion of members 40 as shown in step 300. Openings 74 are sized to allow for insertion and retention of members 40 in platform 75 prior to expansion of balloon 72 while allowing for their detachment from the platform upon their penetration into the intestinal wall. Support platform 75 can then be positioned within a carrying structure 76 as shown in step 301. Carrying structure 76 may correspond to a well structure 76 having side walls 76s and a bottom wall 76b which define a cavity or opening 76c. Platform 75 is desirably attached to inside surface of bottom wall 76b using adhesive or other joining methods known in the art. Well structure 76 can comprise various polymer materials and may be formed using vacuum forming techniques known in the polymer processing arts. In many embodiments, opening 76o can be covered with a protective film 77 as shown in step 302. Protective film 77 has properties selected to function as a barrier to protect tissue penetrating articles 40 from humidity and oxidation while still allowing tissue penetrating articles 40 to penetrate the film as is described below. Film 77 can comprise various water and/or oxygen impermeable polymers which are desirably configured to be biodegradable in the small intestine and/or to pass inertly through the digestive tract. It may also have a multi-ply construction with particular layers selected for impermeability to a given substance, e.g., oxygen, water vapor etc. In use, embodiments employing protective film 77 serve to increase the shelf life of therapeutic agent 101 in tissue penetrating articles 40, and in turn, the shelf life of device 10. Collectively, support platform 75 attached tissue penetrating articles 40, well structure 76, and film 77 can comprise a delivery assembly 78. Delivery assemblies 78 having one or more viable cells or therapeutic agents 101 contained within tissue penetrating article 40 or other viable cells delivery means can be pre-manufactured, stored and subsequently used for the manufacture of device 10 at a later date. The shelf life of assembly 78 can be further enhanced by filling cavity 76c of the sealed assembly 78 with an inert gas such as nitrogen.

Referring back to FIGS. 6A and 6B, assemblies 78 can be positioned on one or both faces 72f of balloon 72. In preferred embodiments, assemblies 78 are positioned on both faces 72f (as shown in FIG. 6A) so as to provide a substantially equal distribution of force to opposite sides of the intestinal wall IW upon expansion of balloon 72. The assemblies 78 may be attached to faces 72f using adhesives or other joining methods known in the polymer arts. Upon expansion of balloon 72, TPAs 40 penetrate through film 77, enter the intestinal wall IW and are retained there by retaining elements 43 and/or other retaining features of tissue penetrating (e.g., an inverse tapered shaft 44t) such that they detach from platform 75 upon deflation of balloon 72.

In various embodiments, one or more of balloons 30, 60 and 72 can be packed inside capsule 20 in a folded, furled or other desired configuration to conserve space within the interior volume 24v of the capsule. Folding can be done using preformed creases or other folding feature or method known in the medical balloon arts. In particular embodiments, balloon 30, 60 and 72 can be folded in selected orientations to achieve one or more of the following: i) conserve space, ii) produce a desired orientation of a particular inflated balloon; and iii) facilitate a desired sequence of balloon inflations. The embodiments shown in FIGS. 5A-5F illustrate an embodiment of a method of folding and various folding arrangements. However, it should be appreciated that this folding arrangement and the resulting balloon orientations are exemplary and others may also be used. In this and related embodiments, folding can be done manually, by automated machine or a combination of both. Also in many embodiments, folding can be facilitated by using a single multi balloon assembly 7 (herein assembly 7) comprising balloons 30, 60, 70; valve chamber 58 and assorted connecting tubing 62 as is shown in the embodiments of FIGS. 3A and 3B. FIG. 3A shows an embodiment of assembly 7 having a single dome construction for balloon 30, while FIG. 3B shows the embodiment of assembly 7 having dual balloon/dome configuration for balloon 30. Assembly 7 can be fabricated using a thin polymer film which is vacuum-formed into the desired shape using various vacuum forming and other related methods known in the polymer processing arts. Suitable polymer films include polyethylene films having a thickness in the range of about 0.003 to about 0.010", with a specific embodiment of 0.005". In preferred embodiments, the assembly is fabricated to have a unitary construction so as to eliminate the need for joining one or more components of the assembly (e.g., balloons 30, 60, etc.). However, it is also contemplated for assembly 7 to be fabricated from multiple portions (e.g., halves), or components (e.g., balloons) which are then joined using various joining methods known in the polymer/medical device arts.

Figure 5A:
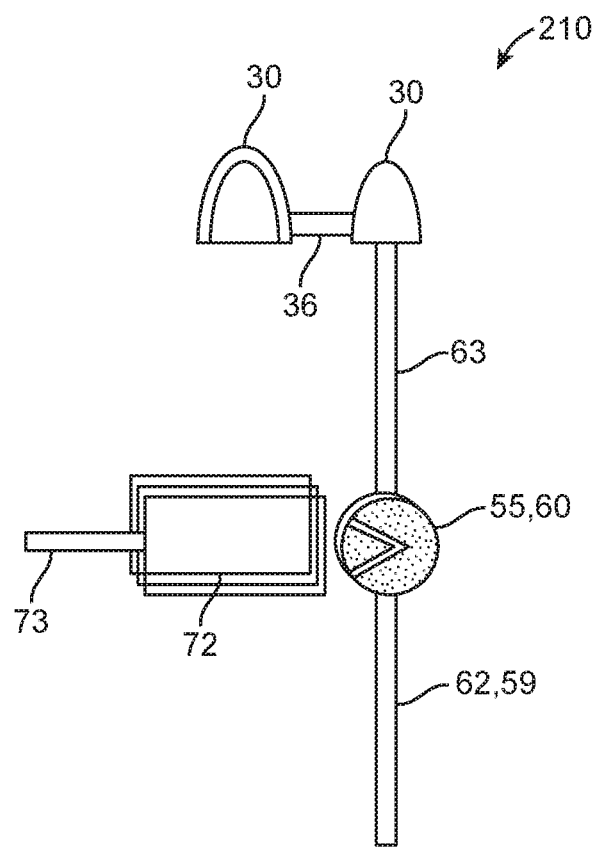
FIGS. 5A-5G are lateral views illustrating a method for folding of the multiple balloon assembly, the folding configuration in each figure applies to both single and dual dome configurations of the deployment balloon, with the exception that FIG. 5C, pertains to a folding step unique to dual dome configurations.
Figure 5B:
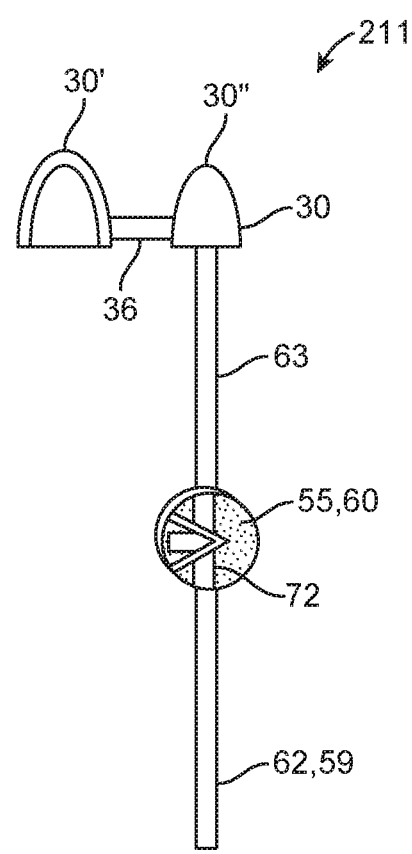
Figure 5C:
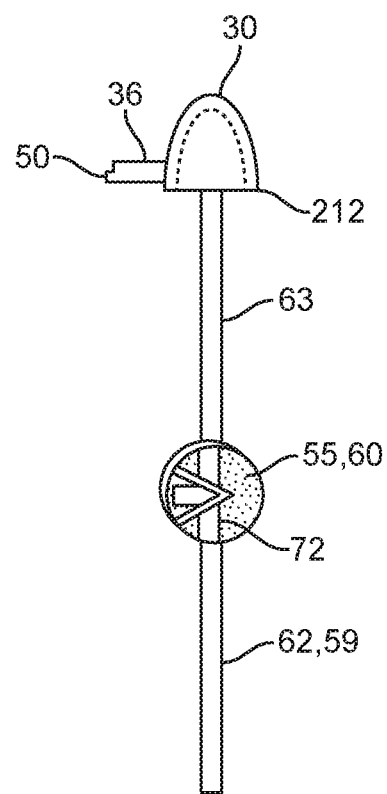
Figure 5D:
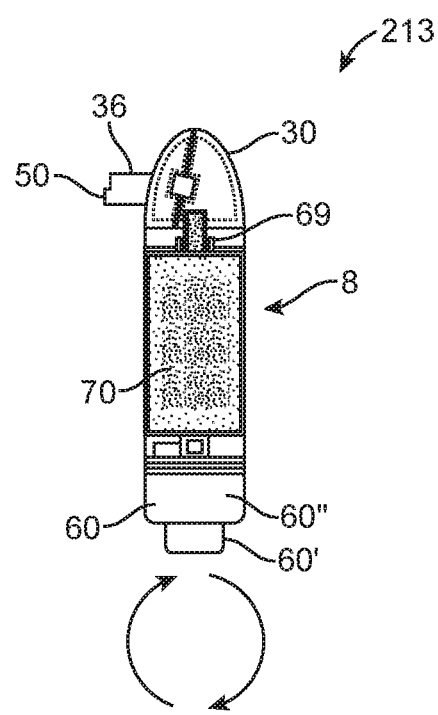
Figure 5E:
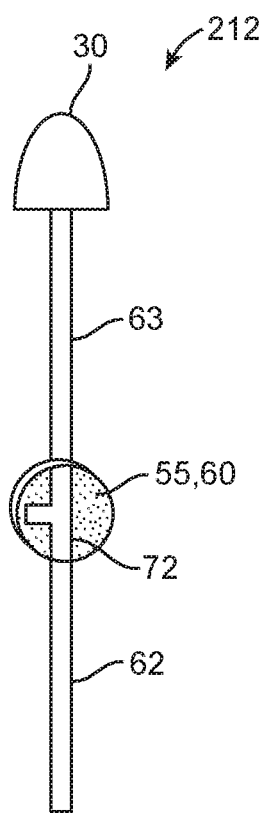
Figure 5F:
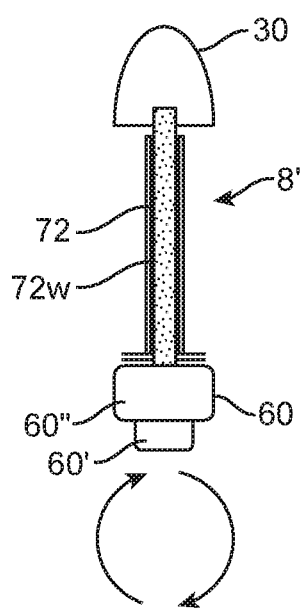
Figure 5G:
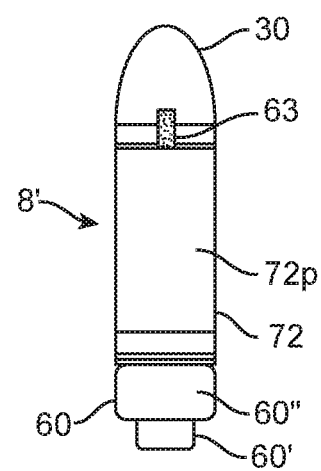

Referring now to FIGS. 5A-5F, 6A-B and 7A-7B, in a first folding step 210, balloon 60 is folded over onto valve fitting 58 with balloon 72 being flipped over to the opposite side of valve fitting 58 in the process (see FIG. 5A). Then in step 211, balloon 72 is folded at a right angle to the folded combination of balloon 60 and valve 58 (see FIG. 5B). Then, in step 212 for dual dome embodiments of balloon 30, the two halves 30' and 30" of balloon 30 are folded onto each other, leaving valve 50 exposed (see FIG. 5C, for single dome embodiments of balloon 30, is folded over onto itself see FIG. 5E). A final folding step 213 can be done whereby folded balloon 30 is folded over 180° to the opposite side of valve fitting 58 and balloon 60 to yield a final folded assembly 8 for dual dome configurations shown in the FIG. 5E and a final folded assembly 8' for single dome configurations shown in FIGS. 5E and 5F. One or more delivery assemblies 78 are then be attached to assembly 8 in step 214 (typically two the faces 72f of balloon 72) to yield a final assembly 9 (shown in the embodiments of FIGS. 6A and 6B) which is then inserted into capsule 20. After an insertion step 215, the final assembled version of device 10 with inserted assembly 9 is shown FIGS. 7A and 7B.

Figure 10B:
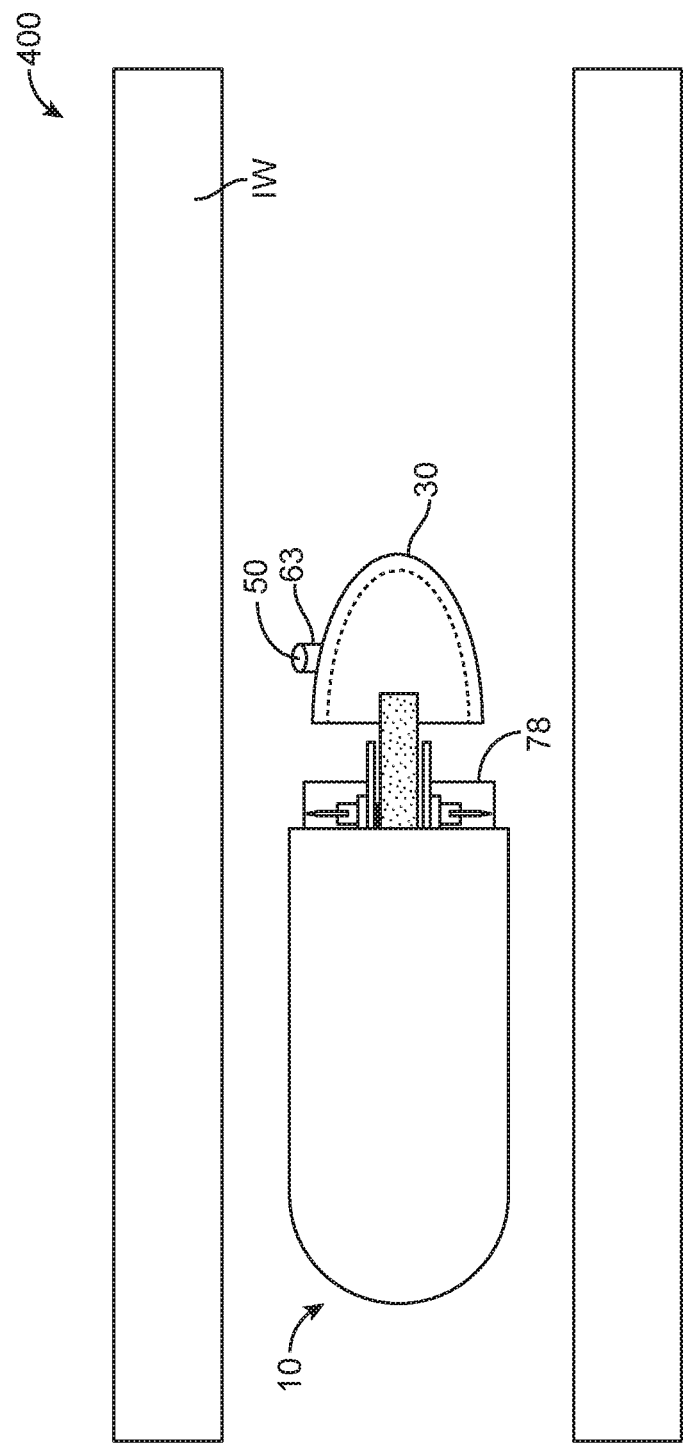
Figure 10C:
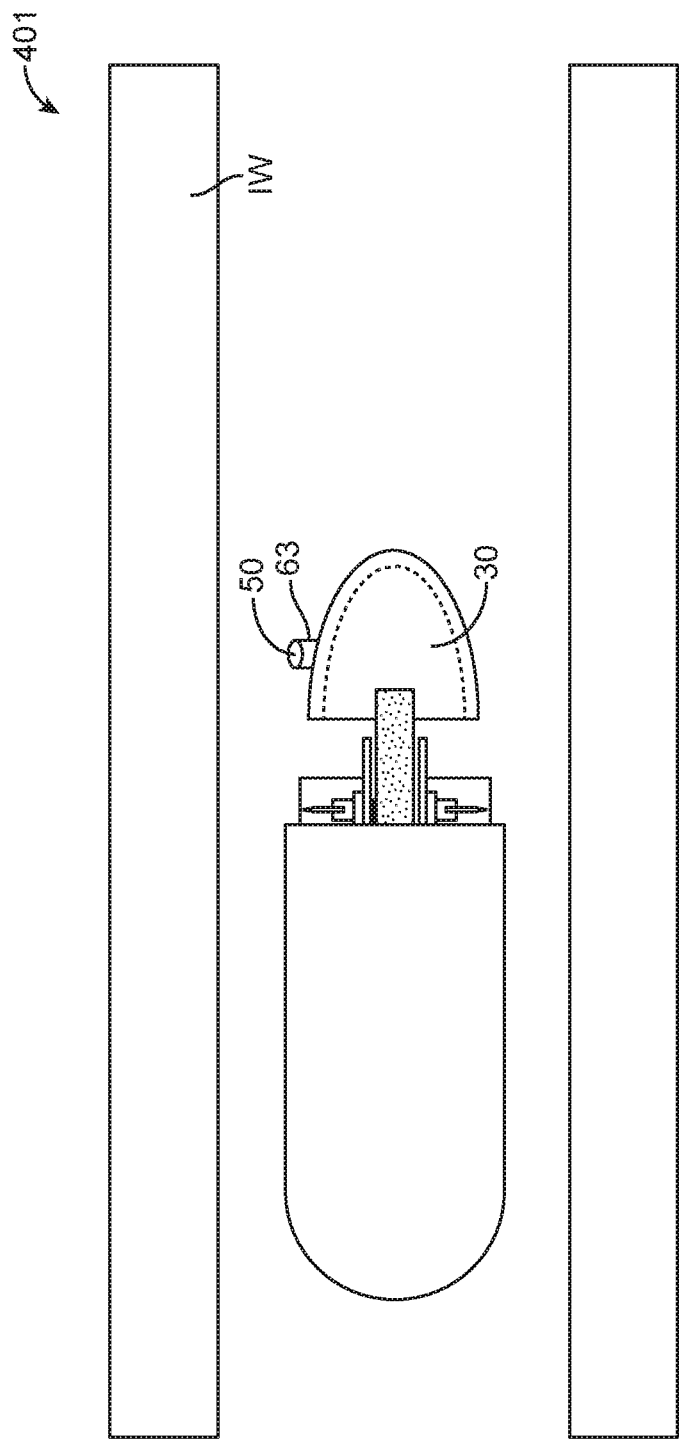
Figure 10D:
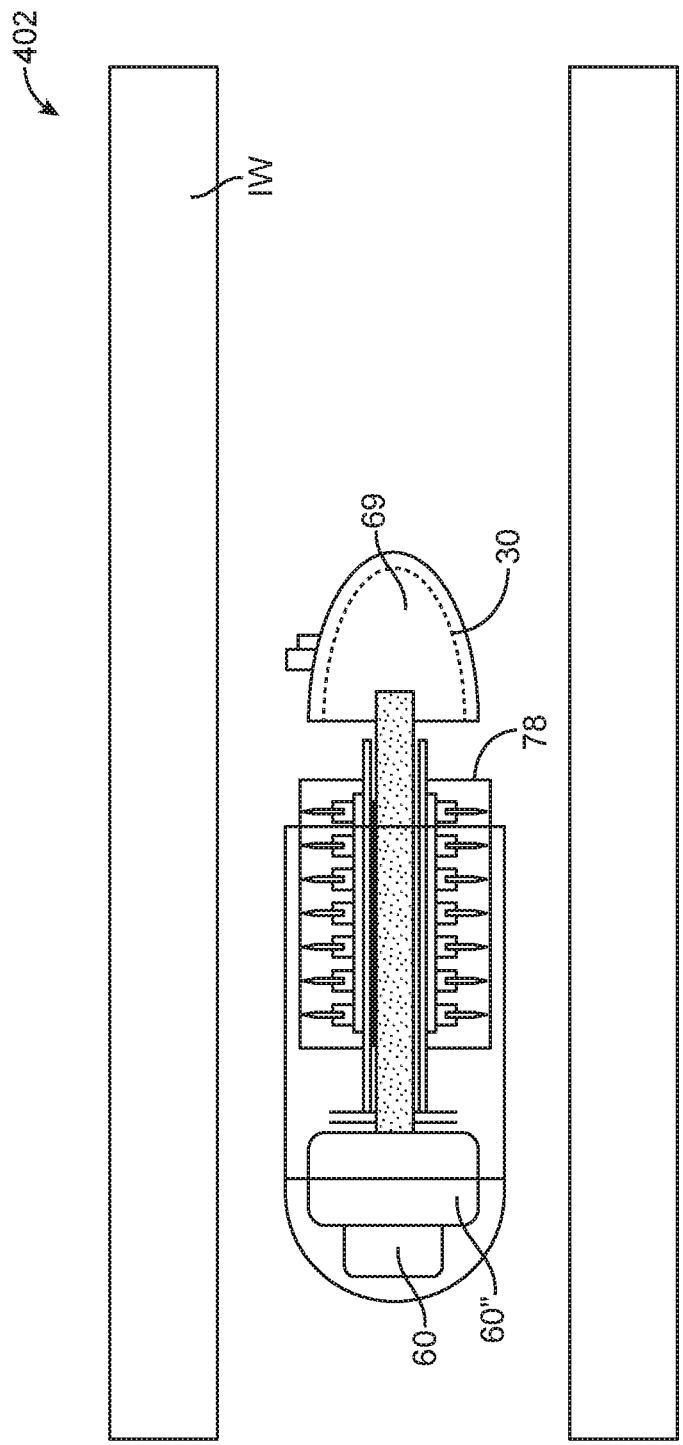
Figure 10E:
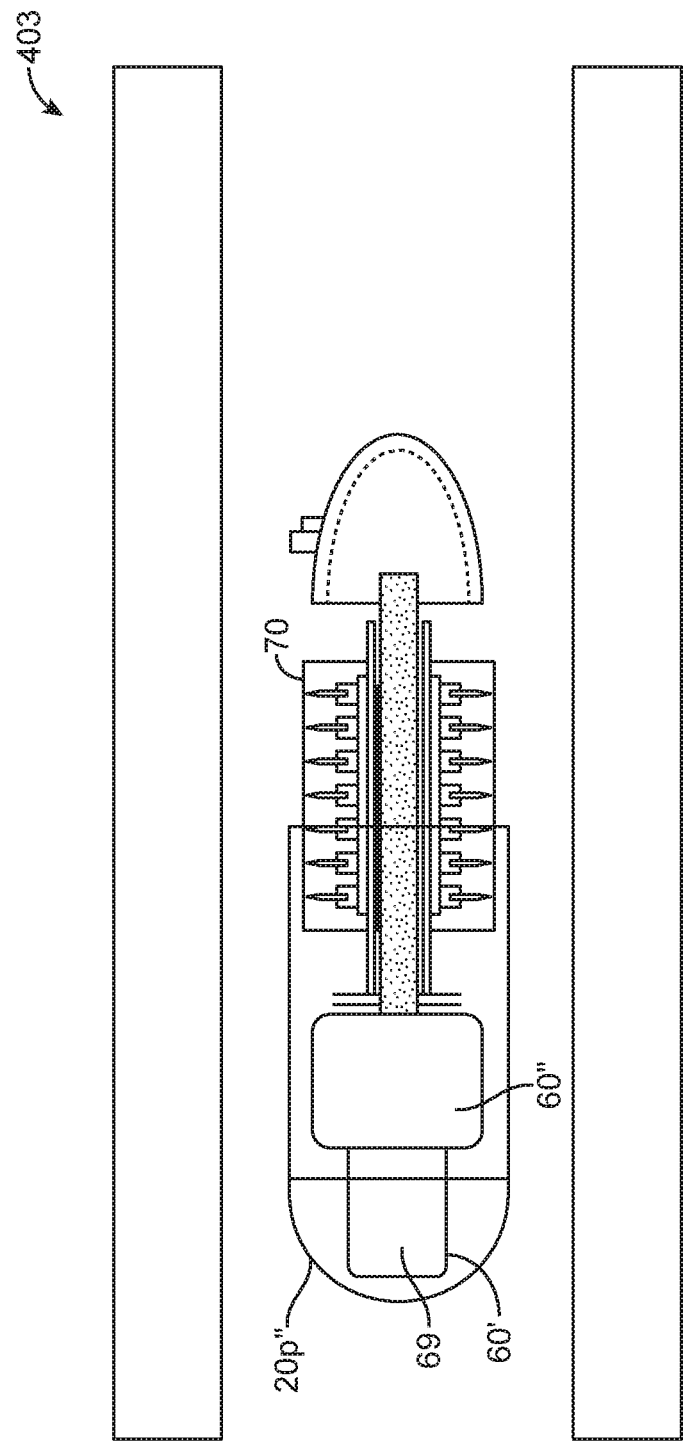
Figure 10F:
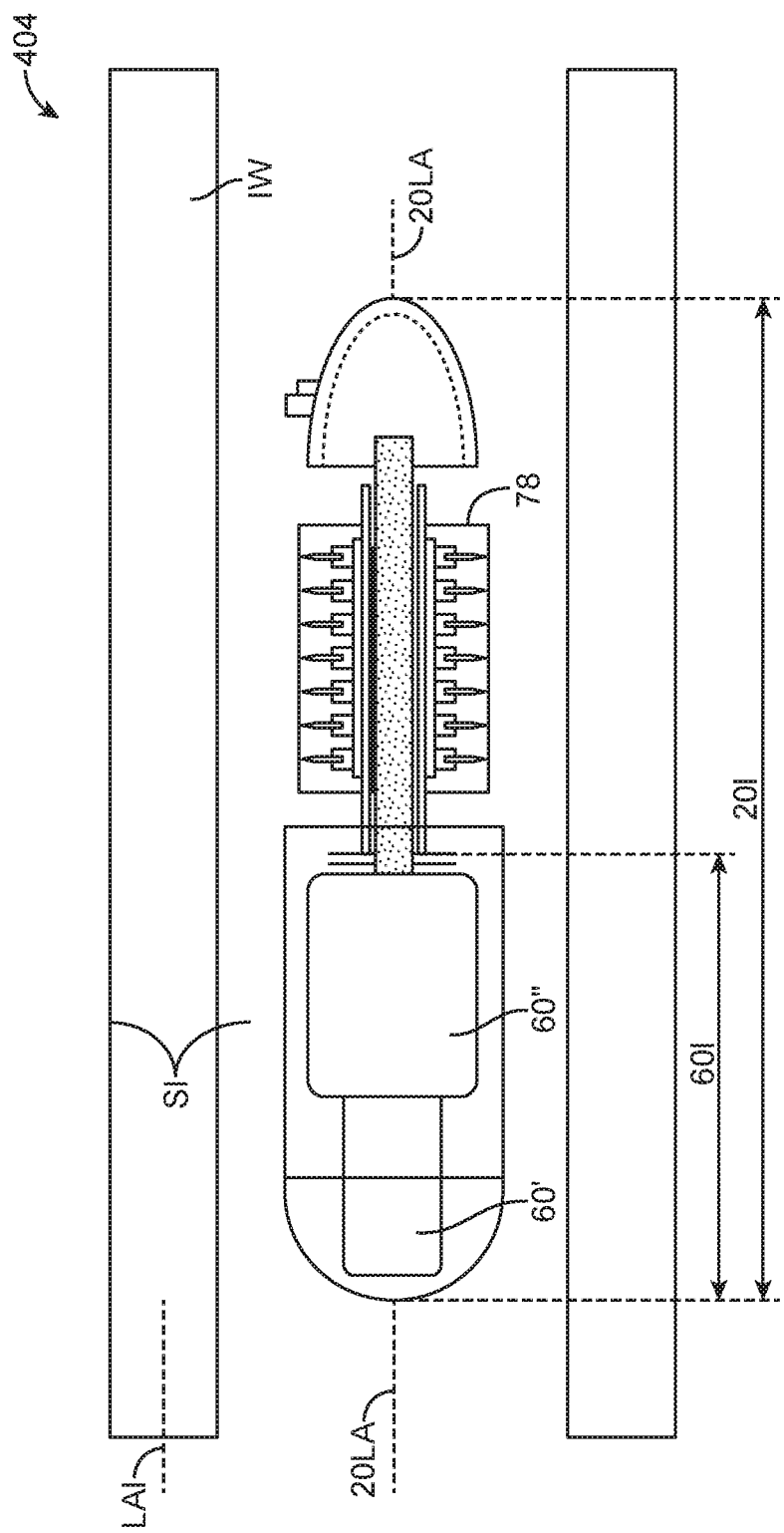
Figure 10G:
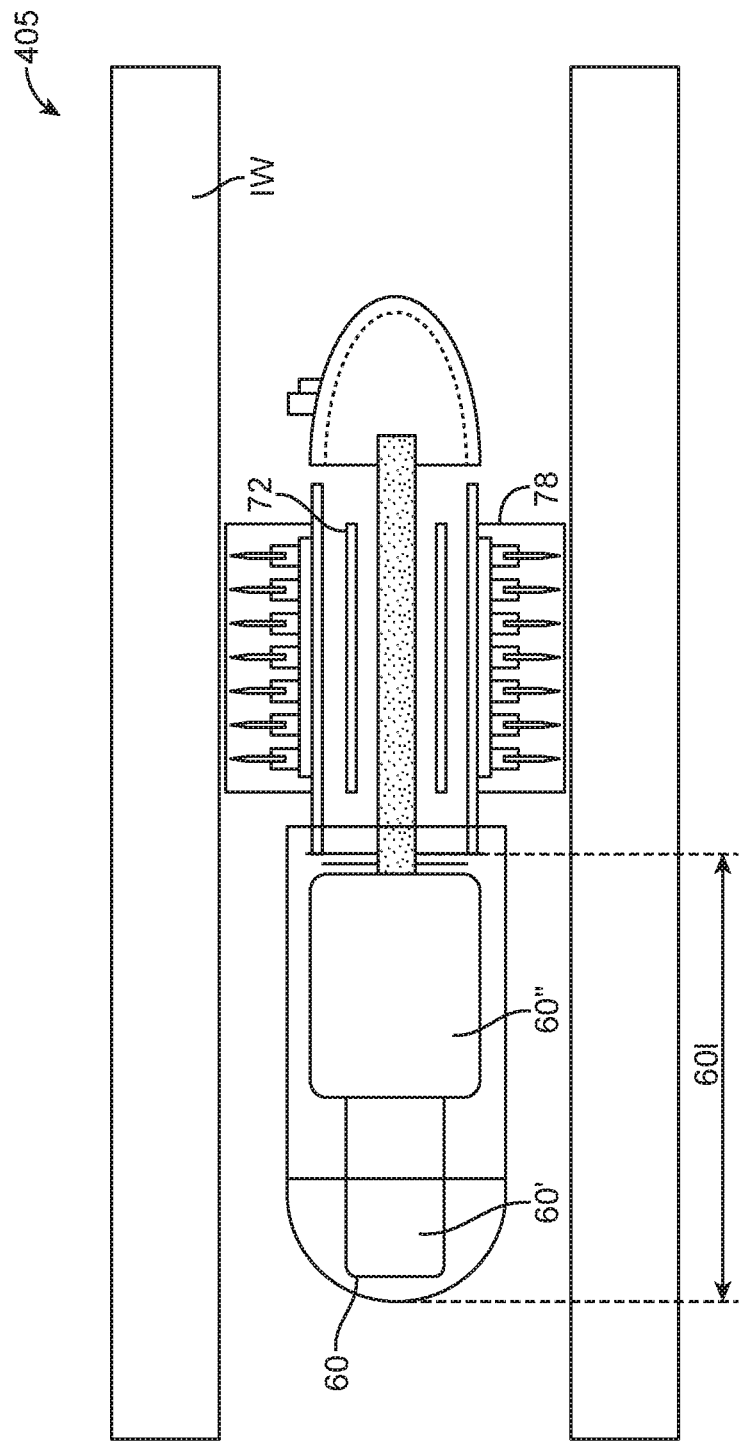
Figure 10H:
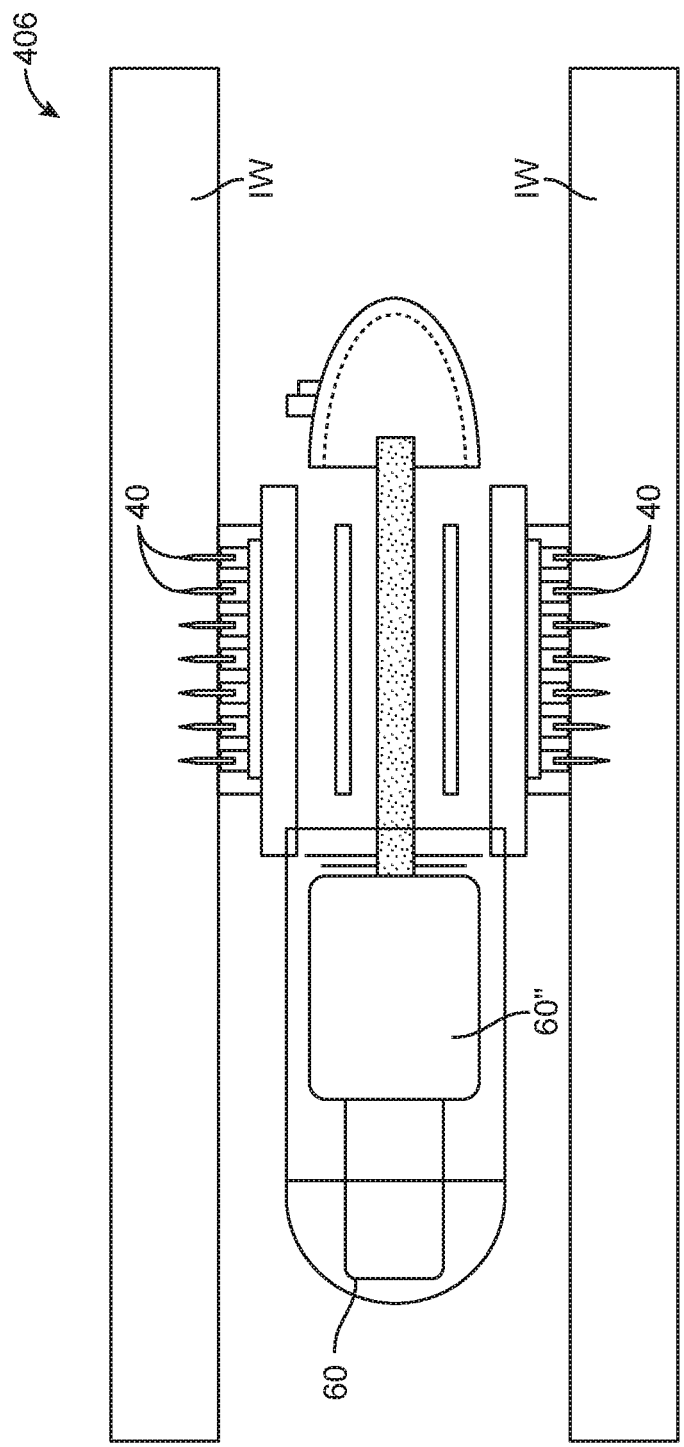
Figure 10I:
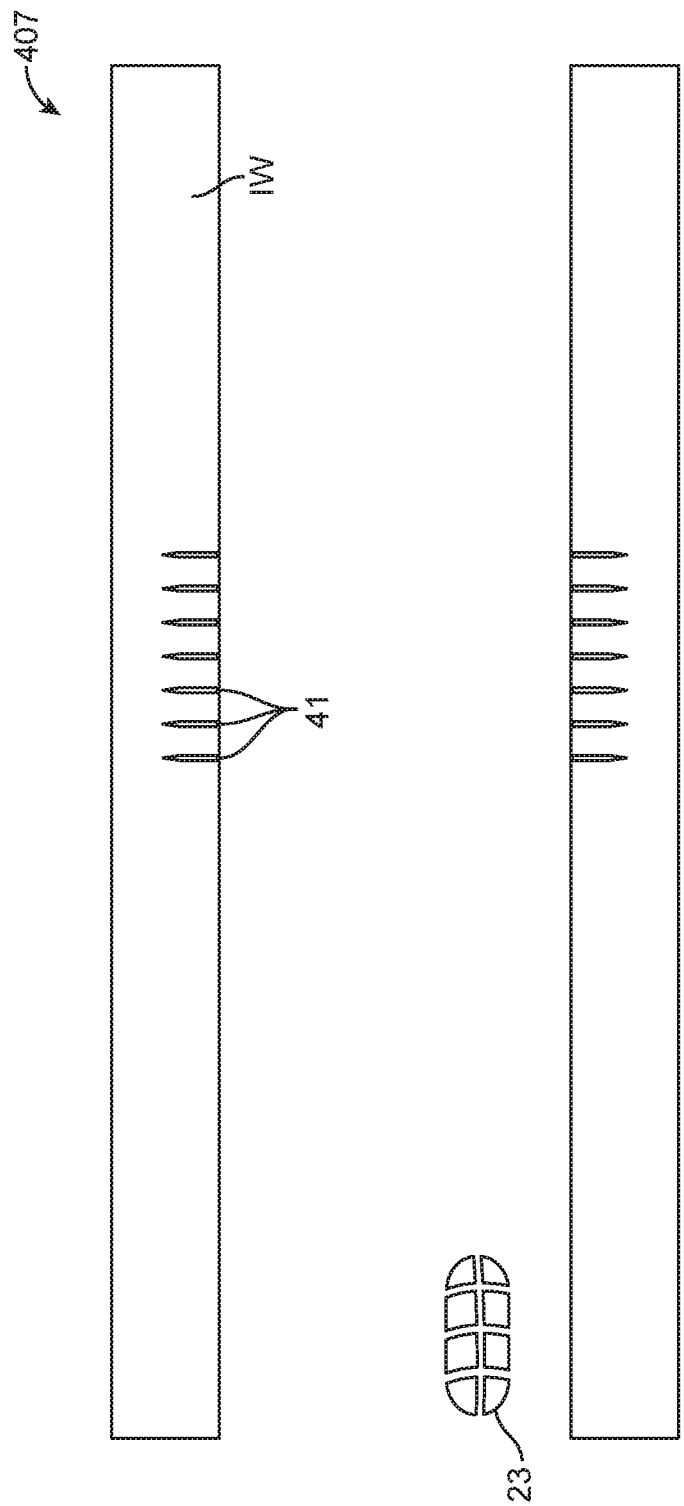

Referring now to FIGS. 10A-10I, a description will be provided of a method of using device 10 to deliver viable therapeutic cells 101 to a site in the GI tract such as the wall of the small or large intestine. It should be appreciated that the steps and there order is exemplary and other steps and orders also contemplated. After device 10 enters the small intestine SI, the cap coating 20c' is degraded by the basic pH in the upper small intestine causing degradation of cap 20p' as shown in step 400 in FIG. 10B. Valve 50 is then exposed to fluids in the small intestine causing the valve to begin degrade as is shown in step 401 in FIG. 10C. Then, in step 402, balloon 30 expands (due to generation of gas 69) as shown in FIG. 10D. Then, in step 403, section 60' of balloon 60 begins to expand to start to push assembly 78 out of the capsule body as shown in FIG. 10E. Then, in step 404, sections 60' and 60" of balloon 60 become fully inflated to completely push assembly 78 out of the capsule body extending the capsule length 201 so as to serve to align capsule lateral axis 20AL with the lateral axis of the small intestine LAI as shown in FIG. 10F. During this time, valve 55 is beginning to fail from the increased pressure in balloon 60 (due to the fact that the balloon has fully inflated and there is no other place for gas 69 to go). Then, in step 405, valve 55 has completely opened, inflating balloon 72 which then pushes the now completely exposed assembly 78 (having been pushed completely out of body 20p") radially outward into the intestinal wall IW as shown in FIG. 10G. Then, in step 406, balloon 72 continues to expand to now advance tissue penetrating articles into the intestinal wall IW as shown in FIG. 10H. Then, in step 407, balloon 72, (along with balloons 60 and 30) has deflated pulling back and leaving tissue penetrating articles retained in the intestinal wall IW. Also, the body portion 20p" of the capsule has completely degraded (due to degradation of coating 20c") along with other biodegradable portions of device 10. Any portion not degraded is carried distally through the small intestine by peristaltic contraction from digestion and is ultimately excreted.

Referring back to FIG. 1B, as an alternative or supplement to the use of pH sensitive degradable coatings and valves for inflation of one or more of balloons 30, 60, and 72 (and deployment of cell preparation 100), in various embodiments the balloons can be expanded responsive to a sensor 97, such as a pH sensor 98 or other chemical sensor which detects the presence of the capsule in the small intestine. Sensor 97 can then send a signal to a controllable embodiment of isolation valve 50 or to an electronic controller 29c coupled to a controllable isolation valve 50 to open and thus expand balloon 30 as is described herein. Embodiments of a pH sensor 98 can comprise an electrode-based sensor or it can be a mechanically-based sensor such as a polymer which shrinks or expands upon exposure to a selected pH or other chemical conditions in the small intestine. In related embodiments, an expandable/contractible pH sensor 98 can also comprise the isolation valve 50 itself, by configuring the sensor to expand or contract about connector 63 and/or 36 so as to open a channel between balloons 30 and 60 and/or compartments 34 and 35.

According to another embodiment for detecting when device 10 is in the small intestine (or other location in the GI tract), sensor 97 can comprise pressure/force sensor such as strain gauge for detecting the number of peristaltic contractions that capsule 20 is being subject to within a particular location in the intestinal tract (in such embodiments capsule 20 is desirably sized to be gripped by the small intestine during a peristaltic contraction). Different locations within the GI tract have different number of peristaltic contractions. For example, the small intestine has between 12 to 9 contractions per minute with the frequency decreasing down the length of the intestine. Thus, according to one or more embodiments, detection of the number of peristaltic contractions can be used to not only determine if capsule 20 is in the small intestine, but the relative location within the intestine as well. In use, these and related embodiments allow for release of viable therapeutic cells 101 and or cell preparation 100 at a particular location in the small intestine.

Still referring to FIG. 1B, as an alternative or supplement to internal activation of the delivery by device 10 (e.g., using a pH sensitive coatings and/or sensor), in some embodiments, the user may externally send a signal to expand one or more of balloon 30, 60 and 72 to deliver viable therapeutic cells 101 to the intestinal wall. The signal may be sent by means of RF, magnetic or other wireless signaling means known in the art. In various embodiments, external activation can be achieved by use of a controllable isolation valve 50 for example, an RF controlled miniature solenoid valve or other electro-mechanical control valve (not shown). In other embodiments, a controllable isolation valve 50 may correspond to a miniature magnetically valve such as a magnetically controlled miniature reed switch (not shown). Such electromechanical or magnetic-based valves can be fabricated using mems and other micro manufacturing methods. In these and related embodiments, the user can use a handheld communication device 13 (e.g., a hand held RF device such as a cell phone) as is shown in the embodiment of FIG. 1B, to send a receive signals 17 from device 10. In such embodiments, swallowable device may include a transmitter 28 such as an RF transceiver chip or other like communication device/circuitry. Handheld device 13 may not only includes signaling means, but also means for informing the user when device 10 is in the small intestine or other location in the GI tract. The later embodiment can be implemented through the use of logic resources 29 (e.g., a processor 29) coupled to transmitter 28 to signal to detect and singe to the user when the device is in the small intestine or other location (e.g., by signaling an input from the sensor). Logic resources 29 may include a controller 29c (either in hardware or software) to control one or more aspects of the process. The same handheld device can also be configured to alert the user when balloon 30 as well as balloons 52 and 60 have been expanded and the selected cell preparation 100 and viable therapeutic cells 101 have been delivered (e.g., using processor 29 and transmitter 28). In this way, the user is provided confirmation that cell preparation 100 has been delivered. This allows the user to take other appropriate therapeutic agents as well as make other related decisions (e.g., for diabetics to eat a meal or not and what foods should be eaten). The handheld device can also be configured to send a signal to swallowable device 10 to over-ride isolation valve 50 and so prevent, delay or accelerate the delivery of viable therapeutic cells 101. In use, such embodiments allow the user to intervene to prevent, delay or accelerate the delivery of viable therapeutic cells, based upon other symptoms and/or patient actions (e.g., eating a meal, deciding to go to sleep, exercise etc.). The user may also externally expand balloon 30 or expandable member 30 at a selected time period after swallowing the capsule. The time period can be correlated to a typical transit time or range of transit times for food moving through the user's GI tract to a particular location in the tract such as the small intestine.

Figure 11A:
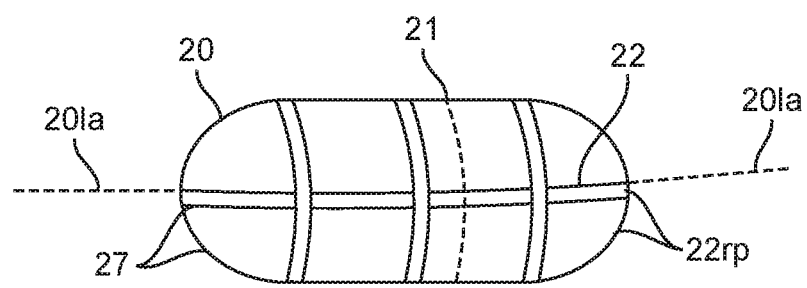
FIG. 11A shows an embodiment of a swallowable viable cells delivery device including a capsule having bio-degradable seams positioned to produce controlled degradation of the capsule in the GI tract.
Figure 11B:
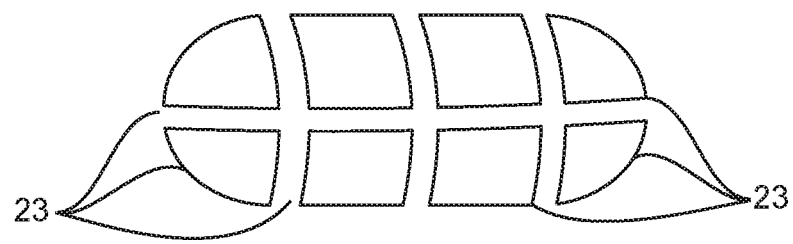
FIG. 11B shows the embodiment of FIG. 11A after having been degraded in the GI tract into smaller pieces.
Figure 16:
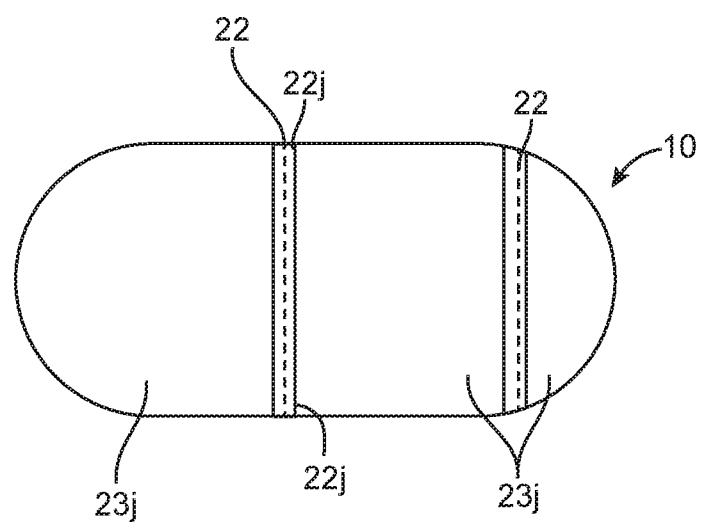
FIG. 16 shows an embodiment of a balloon tearable capsule fabricated from separate portions joined by seams, which can be torn by inflation of the expandable balloon.

Referring now to FIGS. 11A-11B and 16, in various embodiments, the capsule 20 can include seams 22 comprising biodegradable material which controllably degrade to produce capsule pieces 23 of a selectable size and shape to facilitate passage through the GI tract as is shown in the embodiment of FIGS. 11A and 11B. Seams 22 can also include pores or other openings 22p for ingress of fluids into the seam to accelerate biodegradation as is shown in the embodiment of FIG. 16. Other means for accelerating biodegradation of seams 22 can include pre-stressing the seam and/or incorporating degradation nucleation sites in the seams.

Figure 12A:
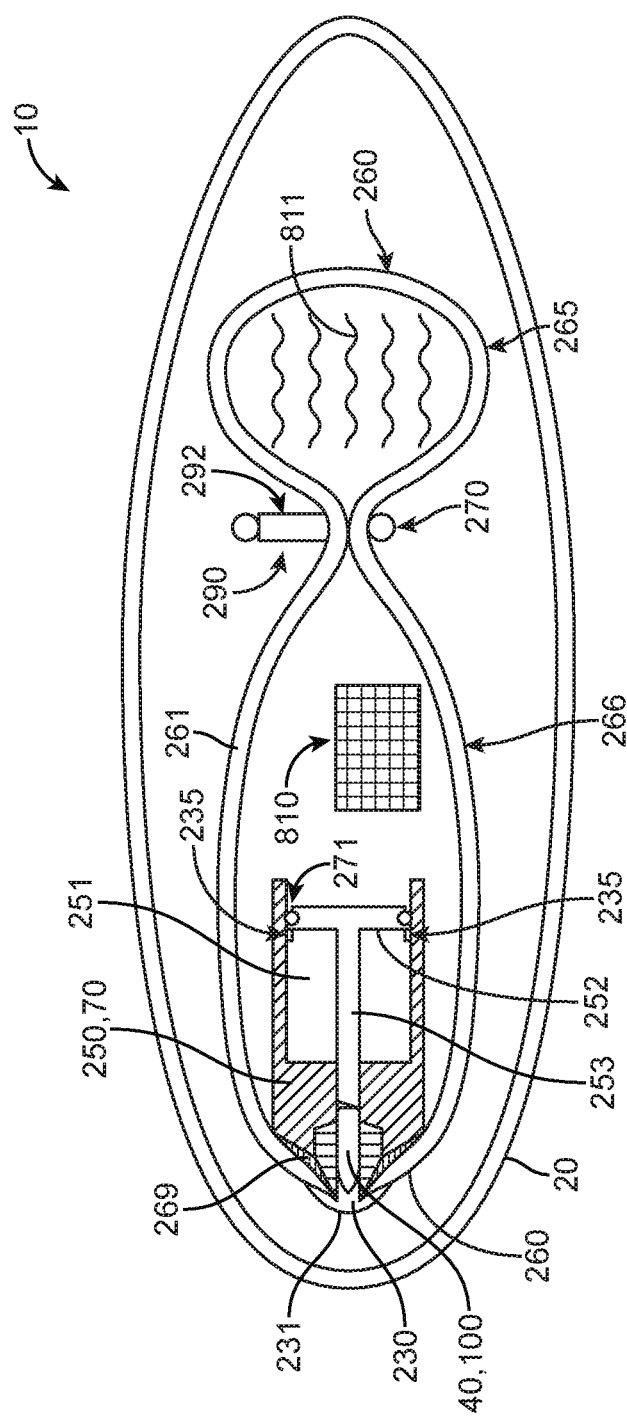
FIGS. 12A-B show an embodiment of a capsule having a piston-cylinder assembly.
Figure 12B:
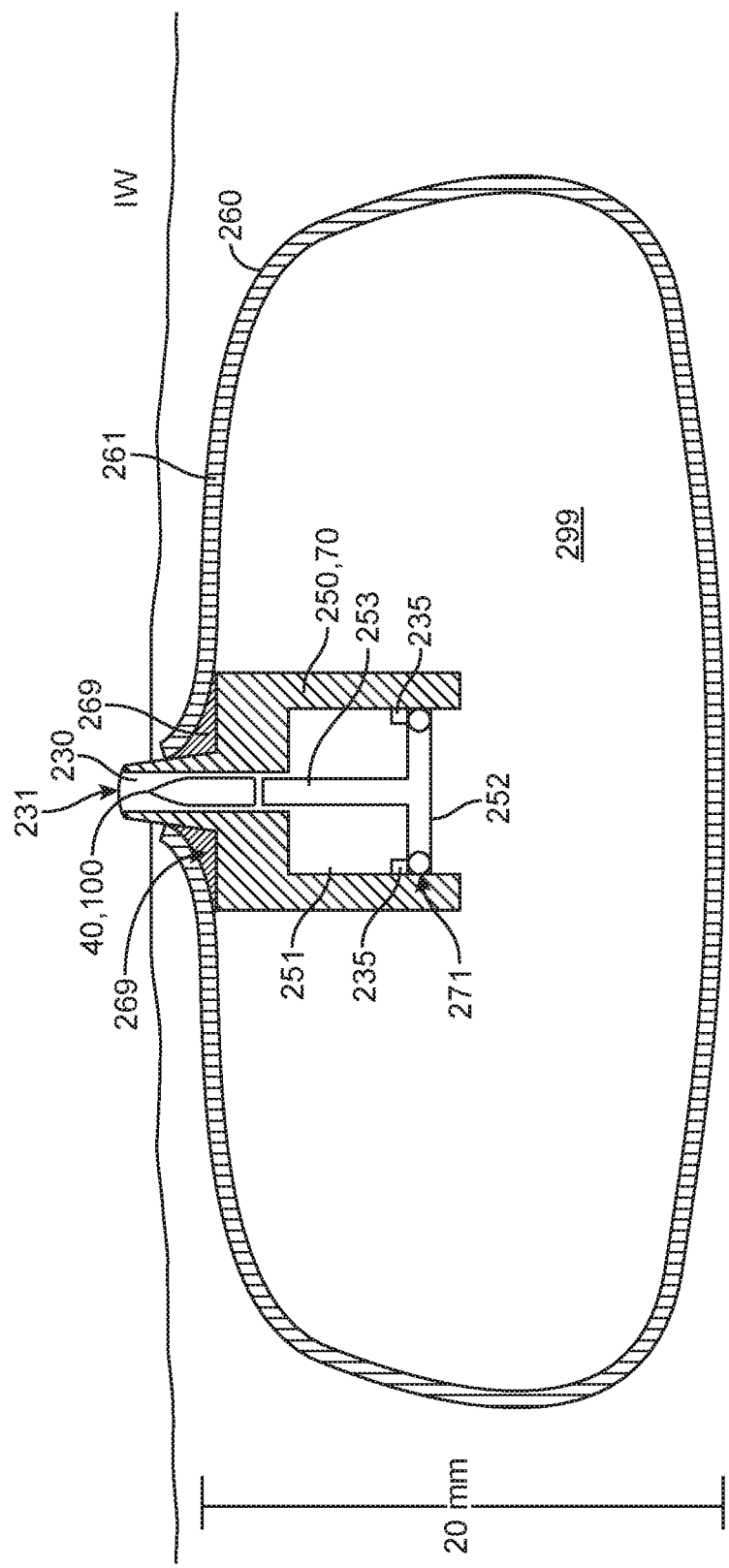
Figure 12C:
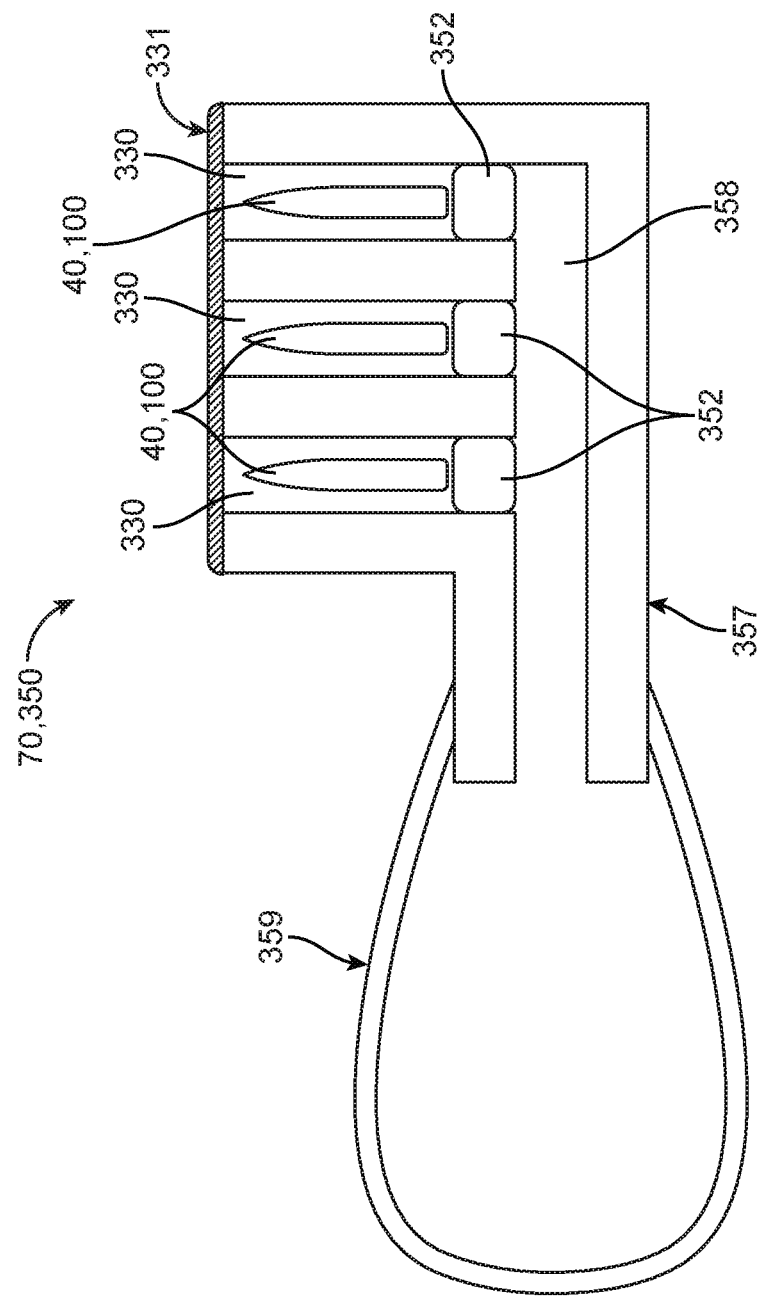
FIG. 12C shows an embodiment of a delivery mechanism having an array of piston-cylinder assemblies.

Referring now to FIGS. 12A-12C, in other embodiments of a swallowable viable cell delivery device 10, the device 10 may include one or more piston cylinder assemblies (PCA) 250 for delivering one or more needles or other tissue penetrating articles (TPA) 40 into the intestinal wall. As such, in these and related embodiments, the piston cylinder assembly (PCA) comprises the delivery mechanism 70. Typically, the piston cylinder assembly (PCA) 250 will be positioned substantially inside a balloon such as balloon 260. However, they may be positioned partially or even completely outside of balloon 260 or other balloon described herein. In some embodiments the balloon 260 comprises multiple portions. As shown in FIG. 12A, the balloon 260 comprises two portions, the first portion comprises a first compartment 265 and the second portion comprises a second compartment 266 separated by a release valve assembly 290. One portion contains a solid reactant 810 such as potassium bicarbonate and the other portions contains a liquid reactant 811 such as citric acid which reacts with the solid reactant to produce a gas 299 such as $CO_2$. The valve assembly 290 comprises an O-ring 270 positioned over a dissolvable pinch valve 292 which pinches down and maintains a seal between the two portions 265 and 266 of the balloon 260. The dissolvable valve is fabricated from maltose or other material which dissolves upon contact with fluid in the small intestine. When that happens, fluid from one portion of the balloon mixes with the reactant in the other to generate the gas 299 to inflate the balloon 260.

Typically, the PCA 250 is positioned in the portion/compartment of the balloon 260 containing the solid reactants (second compartment 266) and is dimensioned accordingly. In one more embodiments, the balloon can have a vertical height between about 12 to 16 mm, with a preferred embodiment of 14 mm, while the inner diameter of the balloon 260 can be in the range of 18 to 22 mm with a preferred embodiment of 20 mm. Other dimensions are also contemplated. In various embodiments, all or portion of the PCA 250 is fabricated from materials which can be dissolvable materials such maltose, or methyl cellulose. It can also be fabricated from ABS and other polymers which are inert within the GI tract. In specific embodiments, the outer top portion of the piston can be made of silicone which is mounted on an inner structure, such as a pedestal structure which can be made of ABS.

As shown in FIG. 12A, when uninflated, the PCA 250 is positioned sideways (horizontally) within the balloon 260 (with respect to the lengthwise axis of the balloon), but when the balloon 260 is inflated the PCA 250 re-orients itself to a vertical position as shown in FIG. 12B. This reorientation can be achieved by virtue of conformation/shape changes once the balloon 260 is inflated as well as by means of an adhesive or other joint 269 attached the PCA 250 to the balloon wall 261 which can be configured to exert a force on the PCA 250 to bias it into a vertical orientation (ie., the joint is made when the PCA 250 is in a vertical position and then the PCA is put into a horizontal position). The joint 269 may comprise various elastic materials known in the art including silicone. The PCA comprises a piston 252 and piston rod 253 which are positioned inside a cylinder 251 (aka piston cylinder). The needle or TPA 40 sits above the piston rod 253 within a needle lumen 230 which is continuous with the piston cylinder. The needle lumen can also include a covering 231 (herein needle lumen covering) which can comprise a foil or polymer film. The ratio in diameter between the piston and piston rod can be selected to result in desired pressure concentration effect (e.g., 2:1, 3:1, etc) from the decrease in surface area. An O-ring 271 is positioned between the piston 252 and the piston cylinder 251 to maintain a seal between the piston 252 and the wall of the piston cylinder 251. Also, a pressure sensitive release 235 is positioned inside the cylinder 251 to keep the piston 252 in place until desired pressure (also referred to as a pressure threshold) has built up (e.g., 5 to psi 20 psi, more preferably 8 to 10 psi) inside balloon 260. The release 235 may correspond to a tab, latch or an O-ring. In use, this release serves to assure that there is sufficient pressure within the balloon to drive the needle 40 a desired depth into the wall of the small intestine (IW).

When the valve separating the two portions (265 and 266) of the balloon 260 dissolves and the balloon begins to inflate, the PCA 250 re-orients itself from a horizontal to vertical orientation as described above. Then, when the pressure in the balloon 260 exceeds the release pressure of the release tab, the piston rod advances against the needle (or other TPA) to force the needle 40 out of the needle lumen 230 and into the wall of the small intestine. Once the needle passes through the needle lumen into the intestinal wall, the balloon 260 then deflates via the now open needle lumen. After needle deployment, the PCA 250 either dissolves or passes harmlessly through the GI tract.

In one or more embodiments, the delivery mechanism 70 can comprise an array 350 of the PCAs (multiple needle PCA) that can be configured for the delivery of multiple needles 40 (or other TPA) as shown in FIG. 12C. In these and related embodiments, the PCAs can include a common inflation manifold 357 coupled to multiple needle lumens 330 via central lumen 358 at one end and to the balloon 359 at the other. Various embodiments of a multiple needle PCA 350 can be configured to deliver from 2 to 6 needles or more. Each needle may contain the same or different viable cells or other therapeutic agent.

As described above, deflation of the delivery balloon 260 occurs through the needle lumen once the needle has been delivered into tissue with no additional means for balloon deflation needed.

Figure 12D:
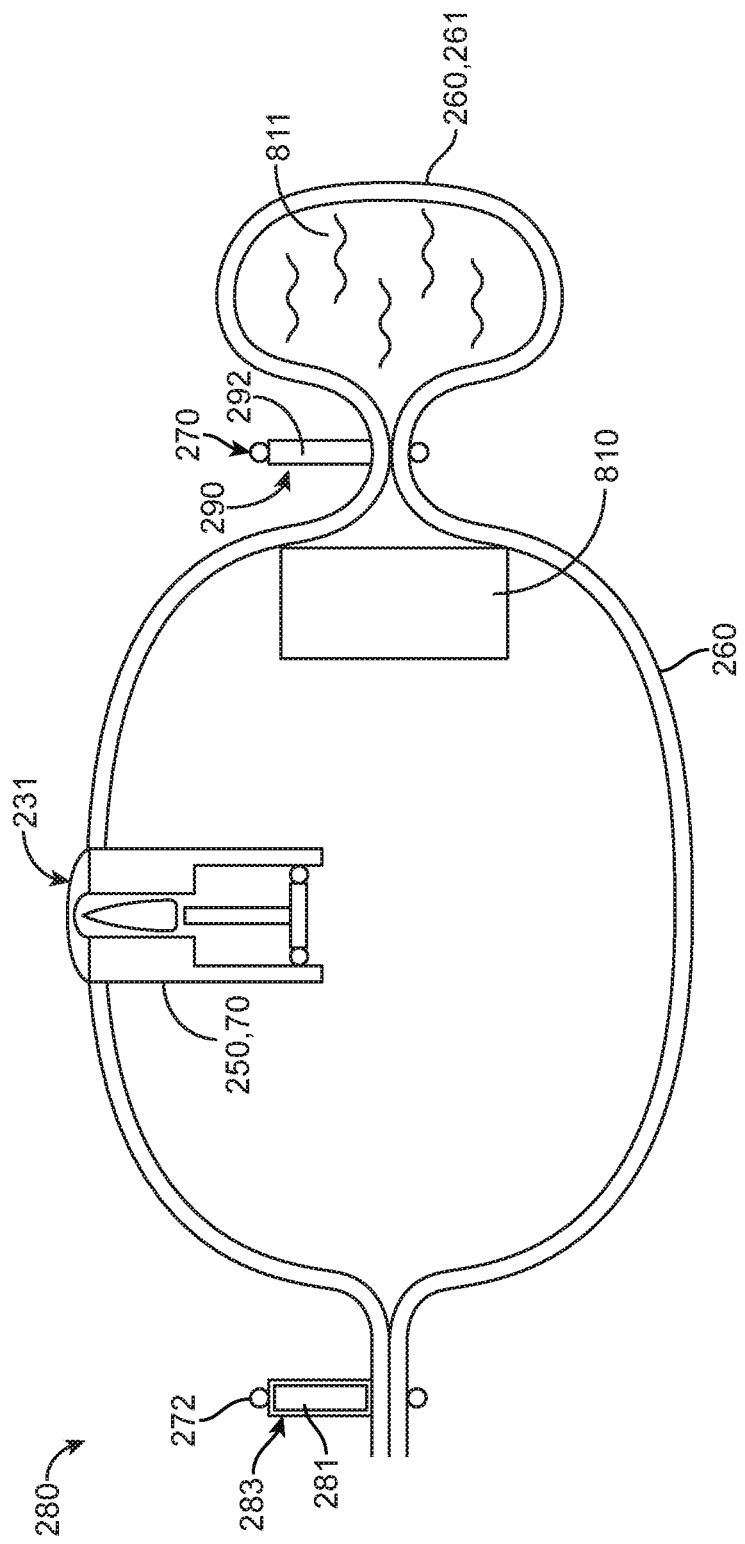
FIG. 12D shows an embodiment of a capsule having a piston-cylinder assembly and a deflation valve.

Referring now to FIG. 12D, in alternative embodiments, the delivery balloon 260 may also include a separate deflation valve assembly 280 which serves as backup or secondary means for deflation in addition to the needle lumen 230. As shown in FIG. 12D, the deflation valve assembly comprises an O-ring 272 positioned over a dissolvable pinch valve 281 which pinches down an open end of the delivery balloon 260. The valve includes a dissolvable body portion made of maltose or other similar material as the release valve and an outer coating such as methyl cellulose. The outer coating 283 is configured to take a substantially longer time to dissolve than the dissolvable valve in the release valve assembly such that the deflation valve is not actuated for periods of 10 minutes or longer (preferably 20) after the release valve is actuated. This is to assure that deflation valve is not accuated until well after the needle has been advanced into the intestinal wall.

Figure 13A:
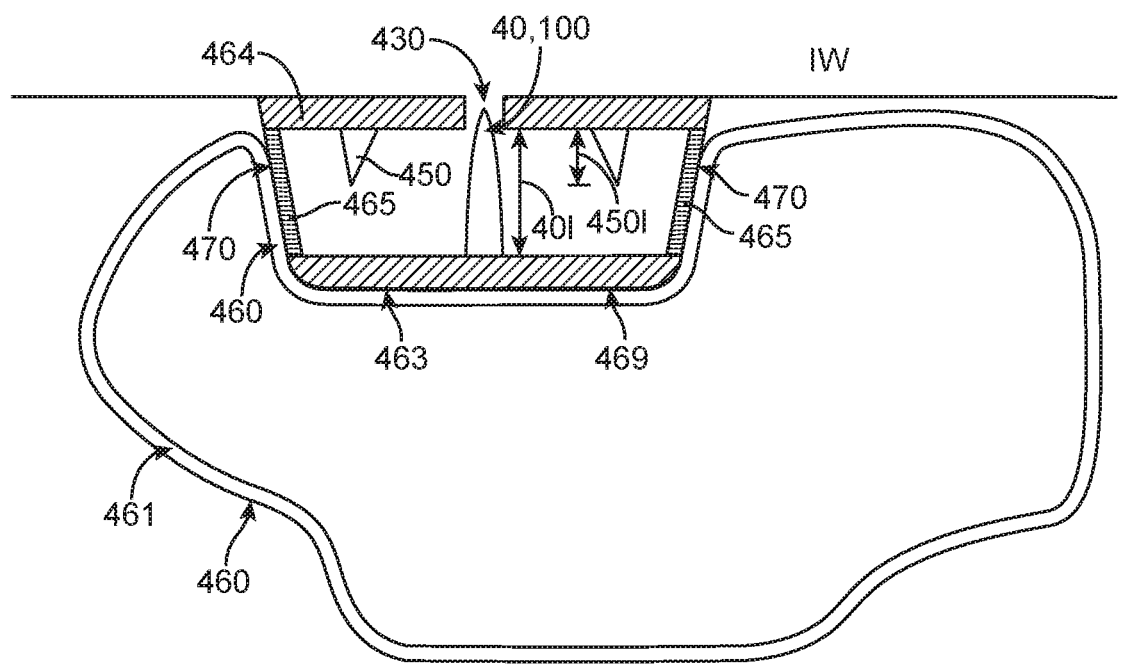
FIG. 13A shows an embodiment of a delivery mechanism having delivery balloon and a delivery compartment.
Figure 13B:
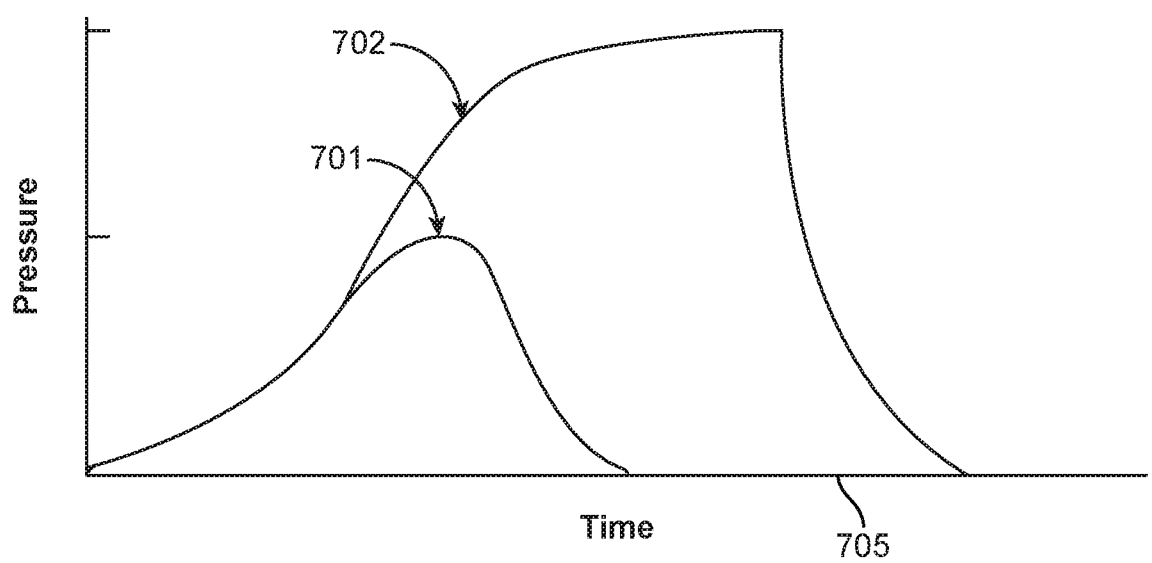
FIG. 13B depicts a balloon inflation pressure curve including a puncture pressure at which the puncture needles puncture the balloon.
Figure 14:
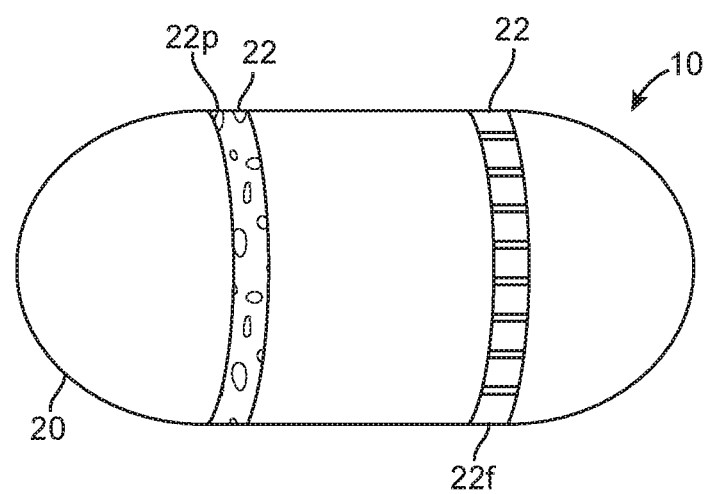
FIG. 14 shows an embodiment of a capsule having biodegradable seams including pores and/or perforations to accelerate biodegradation of the capsule.

Referring now to FIG. 13A-13B, in one or more embodiments of the swallowable device, the delivery balloon 460 can include an assembly configured to both control pressure at which the needle is advanced out of the balloon and into the intestinal wall as well as assure that balloon deflates by means of puncture. The assembly can include a lower portion 463 to which one or more TPAs (herein also referred to as viable cell needles) 40 are attached and an upper portion 464 to which one or more puncture needles (puncture members) 450 are attached. The upper portion may include an aperture 430 or opening for the TPA to be advanced out of the assembly and into the intestinal wall. Upper portion 464 and lower portion 463 may be joined by sidewalls 465. Sidewalls 465 may be collapsible to permit portions 464 and 463 to come together. Sidewalls 465 may have enough rigidity to keep the upper portion 464 and lower portion 463 apart while balloon 460 is not inflating. Sidewalls 465, collapse however under the balloon pressure. The sidewalls may be weakly bonded to the balloon 460 with weak adhesive 470 such that the sidwalls conform to the balloon until the balloon 460 inflates. Upon inflation of balloon 460, the sidewalls 465 separate from the balloon 460. Lower portion 463 may also be bonded to the balloon, but with stronger adhesive adhesive 469. The entire assembly is positioned between the balloon and the intestinal wall IW as shown in FIG. 13A.

Upon inflation of the delivery balloon 460, the puncture needles 450 are configured to penetrate and puncture the lower portion 463 of the delivery assembly and the delivery balloon 460 in order to rupture the delivery balloon. Preferably, the TPA needles 40 have a length 401 sufficiently longer than the length of the puncture needles 4501 such that the TPA 40 is already on its way out of the assembly and even into the intestinal wall before the puncture needles 450 make contact with the lower portion 463 and the balloon 460. According to one or more embodiments, the TPA needle is between 25 to 300% longer than puncture needles with specific embodiments, of 50, 75, 100, 150, 200 and 250%.

According to one or more embodiments, the lower portion 463 is fabricated from a material which does not allow the puncture needle to penetrate until a desired pressure is reached (e.g., 4 to 20 psi, more preferably 8 to 12 psi). This in turn keeps the TPA needle from being completely advanced out into the intestinal wall until the desired pressure is reached. Once the puncture needles 450 penetrate the lower portion 463, they allow the TPA needle 40 to be completely advanced out, while simultaneously puncturing the inflated balloon 460 to ensure deflation. These and related embodiments provide the benefit of both controlling the pressure at which the TPA needle 40 is advanced, assuring that the balloon is deflated.

FIG. 13B shows the Balloon Inflation Pressure (BIP) 702 and the puncture needle pressure (PNP) 701, the pressure used to advance the puncture needles to penetrate balloon 460 and lower portion 463, as time progresses. The PNP rises and peaks as the puncture needles begin to penetrate the lower portion 463. Once penetration of the lower portion 463 and balloon 460 is complete PNP drops to zero. After the TPA needle 40 has been fully inserted into the intestinal wall the gas inside the balloon 460 is able to escape out of aperture 430 and BIP drops to zero as the balloon 460 deflates. In various embodiments, the entire assembly can be fabricated from various biodegradable or inert polymers know in the art. The pressure at which the lower portion 463 is penetrated can be controlled by one or more of the thickness and materials for the lower portion 463. In various embodiments, the lower portion 463 can be fabricated from a polymer film including various inert (acrylonitrile butadiene styrene (ABS)) and/or biodegradable polymer films known in the art (e.g., methylcellulose).

According to one or more embodiments, the TPA needle or other tissue penetrating article 40 can be fabricated from methyl cellulose polymers. Such methyl cellulose polymers can include hydroxy methyl cellulose, carboxy methyl cellulose and various polymer thereof. The advantages of the use of such methyl cellulose polymers for fabrication of the TPA needle (or other tissue penetrating article) compared to maltose-based TPA needles include little or no sensitivity to humidity during storage, reduced wall thickness, smaller needle size with the same viable cells payload, and ability to process the needle after fabrication including processing such as grinding, sharpening, sanding and other related processes. In one or more embodiments, a methyl cellulose-based TPA needle may have a wall thickness in the range of 0.05 to 0.15 mm with a specific embodiment of 0.1 mm. Also in one more embodiments, the methyl celluolse-based TPA needle may carry between 25-150% more viable cells versus a same sized maltose-based TPA. In a specific embodiment of a TPA needle having an outer diameter of 1.5 mm, the methyl cellulose needle can carry 100% more viable cells versus a maltose-based needle.

Referring now to FIGS. 15A-15B and 16, in many embodiments seams 22 can also be configured and arranged so as to allow capsule 20 to be broken into smaller pieces by the inflation of balloon 30 or other expandable member 30. In particular embodiments, seams 22 can be oriented with respect to capsule radial perimeter 21, including having a radial pattern 22rp so as to have the capsule break into halves or other fractional pieces along its perimeter. Seams 22 may also be longitudinally-oriented with respect to capsule lateral access 201a to have the capsule break up into lengthwise pieces.

As an alternative or additional approach for breaking up capsule 20 by balloon inflation (or expansion of other expandable member 30), capsule 20 can be fabricated from two or more separate joinable pieces 23j (e.g., radial halves) that are joined at a joint 22j formed by seams 22 (which function as an adhesive joint) as shown in the embodiment of FIG. 16. Alternatively, joinable pieces 23j may be merely joined by a mechanical fit such as a snap or press fit.

Suitable materials for seams 22 can include one or more biodegradable materials described herein such as PLGA, glycolic acid etc. Seams 22 can be attached to capsule 20 using various joining methods known in the polymer arts such as molding, hot melt junctions, etc. Additionally for embodiments of capsule 20 which are also fabricated from biodegradable materials, faster biodegradation of seam 22 can be achieved by one or more of the following: i) fabricating the seam from a faster biodegrading material, ii) pre-stressing the seam, or iii) perforating the seam. The concept of using biodegradable seams 22 to produce controlled degradation of a swallowable device in the GI tract can also be applied to other swallowable devices such as swallowable cameras (or other swallowable imaging device) to facilitate passage through the GI tract and reduce the likelihood of such a device becoming stuck in the GI tract. Accordingly, embodiments of biodegradable seam 22 can be adapted for swallowable imaging and other swallowable devices.

In still other embodiments, seam 22 can be constructed of materials and/or have a structure which is readily degraded by absorption of ultrasound energy, e.g. high frequency ultrasound (HIFU), allowing the capsule to be degraded into smaller pieces using externally or endoscopically (or other minimally invasive method) administered ultrasound.

Another aspect of the invention provides methods for the delivery of viable cells 101 and other therapeutic agents (into the walls of the GI tract using one or more embodiments of swallowable viable cell delivery device 10. An exemplary embodiment of such a method will now be described. The described embodiment of viable cells delivery occurs in the small intestine SI. However, it should be appreciated that this is exemplary and that embodiments of the invention can be used for delivering viable cells in a number of locations in the GI tract including the stomach and the large intestine. For ease of discussion, the swallowable viable cells delivery device 10 will sometimes be referred to herein as a capsule. As described above, in various embodiments device 10 may be packaged as a kit 14 within sealed packaging 12 that includes device 10 and a set of instructions for use 15. If the patient is using a handheld device 13, the patient may be instructed to enter data into device 13 either manually or via a bar code 18 (or other identifying indicia 18) located on the instructions 15 or packaging 12. If a bar code is used, the patient would scan the bar code using a bar code reader 19 on device 13. After opening packaging 12, reading the instructions 15 and entering any required data, the patient swallows an embodiment of the swallowable viable cells delivery device 10. Depending upon the viable cells, the patient may take the device 10 in conjunction with a meal (before, during or after) or a physiological measurement such as a blood glucose measurement. Capsule 20 is sized to pass through the GI tract and travels through the patient's stomach S and into the small intestine SI through peristaltic action as is embodied in device 10 shown in the embodiment of FIG. 1E. Once the capsule 10 is in the small intestine, coatings 20c' and 20c" are degraded by the basic pH in the small intestine (or other chemical or physical condition unique to the small intestine) causing expansion of balloon 30, 60 and 72 or deliver viable therapeutic cells 101 into the wall of the small intestine SI according to one or more embodiments of the invention.

After viable cell delivery, device 10 then passes through the intestinal tract including the large intestine LI and is ultimately excreted. For embodiments having a tearable capsule, the capsule may immediately be broken into smaller pieces by inflation of balloon 30. For embodiments of the capsule 20 having biodegradable seams 22 or other biodegradable portions, the capsule is degraded in the intestinal tract into smaller pieces, to facilitate passage through and excretion from the intestinal tract. In particular embodiments having biodegradable tissue penetrating needles/members 40, should the needle get stuck in the intestinal wall, the needle biodegrades releasing the capsule 20 from the wall.

For embodiments of device 10 including a sensor 97, expansion of balloon 30 or other expandable member 30 can be effectuated by the sensor sending a signal to a controllable embodiment of isolation valve 50 and/or a processor 29/controller 29c coupled to the isolation valve 50. For embodiments of device 10 including external actuation capability, the user may externally expand balloon 30 (as well as balloons 52 and 60) at a selected time period after swallowing the capsule. The time period can be correlated to a typical transit time (e.g., 30 minutes) or range of transit times (e.g., 10 minutes to 2 hrs.) for food moving through the user's GI tract to a particular location in the tract such as the small intestine.

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the device can be sized and otherwise adapted for various pediatric and neonatal applications as well as various veterinary applications. Also those skilled in the art will recognize, or be able to ascertain using no more than routine experimentation, numerous equivalents to the specific devices and methods described herein. Such equivalents are considered to be within the scope of the present invention and are covered by the appended claims below.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A method for orally delivering viable cells to intestinal tissue of a patient, the method comprising:
swallowing a drug delivery device containing a tissue penetrating article which contains a mass of viable cells, wherein the article passes through the gastrointestinal tract with the article intact and the cells remaining viable;
releasing the article from the drug delivery device in response to a condition in the intestine; and
propelling the article to penetrate into the intestinal tissue and release the cells or substances produced by the cells into the intestinal tissue.

2. The method of claim 1, wherein the intestinal tissue is intestinal wall tissue, small intestine wall tissue or peritoneal wall tissue.

3. The method of claim 1, wherein the delivered cells reseed a portion of the mucosa or lining of the small intestine, large intestine, or stomach.

4. The method of claim 1, wherein the condition is a pH or a pH in the small intestine.

5. The method of claim 2, wherein the pH in the small intestine is above about 7.1.

6. The method of claim 1, wherein propelling the article comprises applying a propulsive force by means of the expansion of an expandable member.

7. The method of claim 6, wherein the expandable member is expanded by a chemical reaction triggered in response to a pH in the small intestine or other location in the gastrointestinal tract.

8. The method of claim 1, wherein the cells are in a suspended reanimatable state prior to being ingested by the patient.

9. The method of claim 8, wherein the cells are reanimated after ingestion of the drug delivery device.

10. The method of claim 9, wherein the cells are reanimated by the patient's body temperature.

11. The method of claim 9, wherein the cells are reanimated by conditions in the intestinal tissue including at least one of temperature, blood supply or oxygen supply.

12. The method of claim 8, wherein the cells are frozen prior to being swallowed by the patient.

13. The method of claim 12, wherein the cells at least partially thaw as they pass through the gastro-intestinal tract.

14. The method of claim 1, wherein the cells are protected from conditions of the gastrointestinal tract by a barrier provided by the article.

15. The method of claim 14, wherein the barrier remains intact while the article passes through the gastrointestinal tract and biodegrades within the intestinal tissue.

16. The method of claim 15, wherein the barrier is configured to biodegrade over a time period of at least about 12 hours.

17. The method of claim 16, wherein the time period is in a range from about 1 to 5 days.

18. The method of claim 15, wherein the barrier comprises a biodegradable polymer.

19. The method of claim 18, wherein the biodegradable polymer is selected from a group consisting of poly lactic acid (PLA), poly lactic-co-glycolic acid (PLGA) and maltose.

20. The method of claim 1, wherein the barrier comprises a wall having fenestrations.

21. The method of claim 20, wherein the fenestrations are configured to allow the passage of fluids and molecules but contain the cells and gel, at least a portion of the barrier including fenestrations having a slower rate of biodegradation relative to the rest of the barrier.

22. The method of claim 21, wherein the fenestrations have a width in the range from about 0.5 μm to 5 μm or an area in the range from 0.8 μm² to 80 μm².

23. The method of claim 21, wherein at least a portion of the cells remain in the article and produce a therapeutic compound which diffuses out of the fenestrations.

24. The method of claim 20, where the fenestrations are configured as echogenic markers to allow for location of the barrier in the body using ultrasonic imaging, the method further comprising:
ultrasonic imaging the body of the patient to locate the barrier using the fenestrations.

25. The method of claim 24, where the fenestrations are configured to provide an indication of a degree of biodegradation of the barrier, the method further comprising:
ultrasonic imaging the body of the patient to ascertain a degree of biodegradation of the barrier.

26. The method of claim 1, wherein the cells are present in a viability-sustaining gel.

27. The method of claim 26, wherein the viability-sustaining gel comprises at least one of an alginate, a protein, a glycosaminoglycan, and polysaccharide.

28. The method of claim 26, wherein the viability-sustaining gel is at least partially saturated with oxygen to preserve the viability of the cells.

29. The method of claim 26, wherein the viability-sustaining gel is at least partially saturated with nitrogen or other inert gas to preserve the viability of the cells.

30. The method of claim 1, wherein the viable cells are therapeutic cells, entero-endocrine cells, gastric enteroendocrine cells, or intestinal enteroendocrine cells.

31. The method of claim 30, wherein the viable cells are selected from a group consisting of pancreatic B-cells, L-cells, K-cells, G-cells, I cells, immune cells, stem cells, mesenchymal stem cells, and hematopoietic stem cells.

32. The method of claim 1, wherein once delivered into intestinal tissue, the cells produce a therapeutic compound released within the body.

33. The method of claim 32, wherein the therapeutic compound comprises a glucose regulating compound, insulin, an incretin, or Gastrin.

34. The method of claim 32, wherein at least a portion of the cells remain in the article while producing the therapeutic compound.

35. A method for orally delivering viable cells to intestinal tissue of a patient, the method comprising:
swallowing a drug delivery device containing a tissue penetrating article which contains a mass of viable cells in a suspended reanimatable state, wherein the article passes through the gastrointestinal tract with the article intact and the cells remaining viable;

releasing the article from the drug delivery device in response to a condition in the intestine; and propelling the article to penetrate into the intestinal tissue to release the cells or substances produced by the cells into the intestinal tissue and wherein the cells are reanimated by a condition in the patient's body.

\* \* \* \* \*